(12) United States Patent
Arkoff et al.

(10) Patent No.: US 11,532,393 B2
(45) Date of Patent: Dec. 20, 2022

(54) COMPREHENSIVE HEALTHCARE DATA MANAGEMENT SYSTEM

(71) Applicants: Harold Arkoff, Sudbury, MA (US); Vedran Jukic, Trieste (IT)

(72) Inventors: Harold Arkoff, Sudbury, MA (US); Vedran Jukic, Trieste (IT)

(73) Assignee: OSSI, Sudbury, MA (US)

( * ) Notice: Subject to any disclaimer, the term of this patent is extended or adjusted under 35 U.S.C. 154(b) by 199 days.

(21) Appl. No.: 16/812,282

(22) Filed: Mar. 7, 2020

(65) Prior Publication Data

US 2021/0050104 A1     Feb. 18, 2021

Related U.S. Application Data

(63) Continuation-in-part of application No. 13/651,058, filed on Oct. 12, 2012, now abandoned.

(51) Int. Cl.
| | |
|---|---|
| *G16H 40/67* | (2018.01) |
| *G06Q 10/06* | (2012.01) |
| *G06Q 10/10* | (2012.01) |
| *G16H 40/20* | (2018.01) |

(52) U.S. Cl.
CPC ............ *G16H 40/67* (2018.01); *G06Q 10/06* (2013.01); *G06Q 10/1095* (2013.01); *G16H 40/20* (2018.01)

(58) Field of Classification Search
CPC ........ G16H 40/67; G16H 40/20; G06Q 10/06; G06Q 10/1095
USPC ....................................................... 705/2–3
See application file for complete search history.

(56) References Cited

U.S. PATENT DOCUMENTS

| | | | | | |
|---|---|---|---|---|---|
| 4,937,743 | A | * | 6/1990 | Rassman ................ | G06Q 10/06 345/441 |
| 5,842,173 | A | * | 11/1998 | Strum .................... | G16H 40/67 705/2 |
| 2002/0040313 | A1 | * | 4/2002 | Hunter ................... | G06Q 10/06 705/7.13 |
| 2002/0165732 | A1 | * | 11/2002 | Ezzeddine ............. | H04L 51/38 705/2 |
| 2006/0004605 | A1 | * | 1/2006 | Donoghue ............. | G06Q 10/10 705/2 |
| 2006/0053034 | A1 | * | 3/2006 | Hlathein ................ | G06Q 10/06 705/2 |

(Continued)

*Primary Examiner* — Michael Tomaszewski
(74) *Attorney, Agent, or Firm* — Michael Razavi; Alfred F. Hoyte, Jr.

(57) ABSTRACT

A comprehensive health care data management system is provided. In an embodiment, a Medical Data Governance System records, secures, and provides appropriate access to all patient data. By concentrating all available relevant medical data into a single source, and providing a subset of data to each receiving subsystem with the correct source and time reference, the Medical Data Governance System becomes the True Source of Data and guarantees the data consistency through the use of block chain signatures. In another aspect of the invention, a system of servers is provided, which communicate data in real time with white boards stationed in the operating rooms of a healthcare facility. Medical personnel and healthcare facility staff members can view the formatted data on a white board and input new or revised data directly on the white board or at an input station near the white board.

14 Claims, 24 Drawing Sheets

(56) References Cited

U.S. PATENT DOCUMENTS

| | | | | |
|---|---|---|---|---|
| 2006/0138211 | A1* | 6/2006 | Lubow | G06K 17/00 235/382 |
| 2010/0082368 | A1* | 4/2010 | Gecelter | G16H 40/20 705/3 |
| 2010/0305970 | A1* | 12/2010 | McLaren | G16H 10/60 705/3 |
| 2010/0306858 | A1* | 12/2010 | McLaren | G16Z 99/00 726/28 |
| 2010/0332255 | A1* | 12/2010 | Rotunda | G16H 40/20 715/753 |
| 2013/0066647 | A1* | 3/2013 | Andrie | G16H 20/40 705/2 |
| 2013/0103768 | A1* | 4/2013 | Freebeck | G16H 40/20 709/204 |
| 2013/0253339 | A1* | 9/2013 | Reyes | G06Q 10/06 600/549 |
| 2013/0257716 | A1* | 10/2013 | Xin | G06F 1/3215 345/156 |
| 2014/0067413 | A1* | 3/2014 | Ghivizzani | G16H 40/20 705/2 |

\* cited by examiner

Figure 19
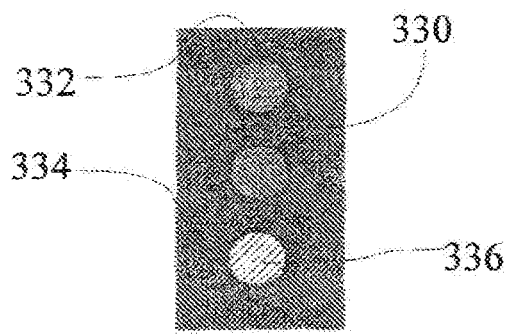
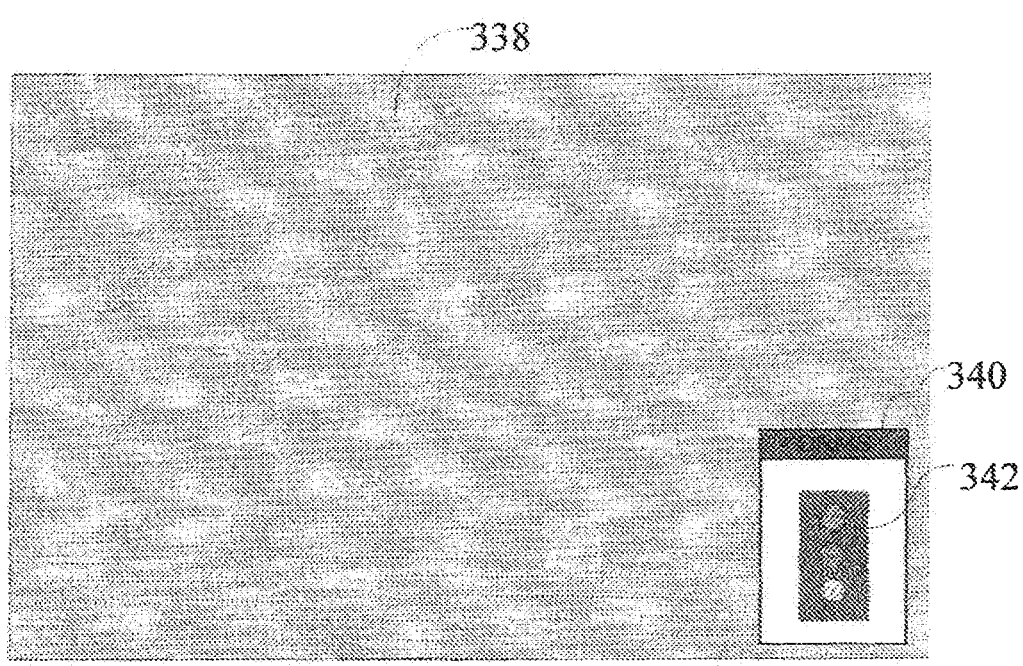
Figure 20

COMPREHENSIVE HEALTHCARE DATA MANAGEMENT SYSTEM

CROSS-REFERENCE TO RELATED APPLICATIONS

This application is a continuation in part of U.S. application Ser. No. 13/651,058, filed on Oct. 12, 2012.

FIELD OF THE INVENTION

This application relates to healthcare data management hardware and software, and more particularly to reliable medical device data intereoperability and storage in a normalized, standardized format useful for healthcare providers and medical research.

BACKGROUND

Modern hospitals are complex, technologically sophisticated organizations having sometimes thousands of employees, doctors, nurses, medical technicians and administrators, with critical life or death decisions being made regularly—and sometimes having to be made abruptly and quickly. Up-to-date, perspicuous and complete data about the patient can make a difference. And even when critical decisions are not at stake, increases in the cost of health care have made it imperative to use patient data, facility personnel and resources as efficiently as possible. Also, particular medical personnel or facility staff members may need to be alerted with respect to the updated status of particular resources or patients and may need to provide updates to the information displayed from where ever they are located.

Medical Data Governance is an approach to managing data that allows hospitals and health organizations to balance two needs: the need to collect and secure all available information while also maximizing the usefulness of that information for patient care, medical research and other valid purposes. Patient data collected during operations, other medical procedures and patient recovery is updated continually and often needs to be displayed immediately and in an efficient and speedily apprehended manner to attending medical personnel as well as being permanently retained in a standard format useful to facility management and medical researchers among others who may be in remote locations and/or need to compare data from myriad healthcare facilities.

Nowadays governments try to limit legal collection of personal data through various privacy protection acts. By doing so, they limit the collection of data for future research or for validation at the time of data collection. Medical Data Governance (MDG) absolves the important role of governing the process of acquisition, patient identification, provider identification, data validation, time synchronization, localization of different, non-homogeneous clinical, medical, medical relevant, and patient relevant data from isolated, standalone medical devices or networked devices. MDG fulfills the need for a true and complete source of data for other consumers of medically relevant data, such as Electronical Medical Records, Health Medical Records, Artificial Intelligence systems, Machine Learning systems, research, trials, Decision Support Systems, data recording and so on. The process of collection, normalization, association of data, along with source localization, type, quality and anonymous metadata, allow customizable subsets of data to be provided to different accredited users, systems and endpoints. Some of the use cases of MDG are innovative, and some represent a more efficient, cost effective methods compared to already existing procedures or methods.

Artificial Intelligence and Machine Learning systems require a medical data governance middleware to assure proper, normalized and verified data inputs. Legacy health information systems and electronical medical records were designed to receive only a portion of the exponentially increasing data medical devices can create and can be collected. Further, outdated HIS/EMR (Healthcare Information Systems/Electronic Medical Record) and inadequate patient identification and association can cause a serious bottleneck for data-hungry personalized medicine, real time applications, and in practice, most medical device data are not recorded at all. And yet as shown in recent studies it can be easy to identify individuals even from anonymized data https://www.nytimes.com/2019/07/23/health/data-privacy-protection.html.

In another aspect of the invention, hospitals and other healthcare facilities providing surgical services must coordinate a myriad of resources, medical personnel, and hospital staff to provide optimum and efficient care to their patients. Information about status of these resources and the facilities' patients must be updated constantly and be available to the relevant medical personnel and facility staff in the operating rooms (ORs) where the surgical services are delivered, in other ancillary rooms of the facility, and to medical personnel and facility staff who may be in remote locations. Particular medical personnel or facility staff members may need to be alerted with respect to the updated status of particular resources or patients and may need to provide updates to the information displayed from wherever they are located.

U.S. Pat. No. 5,842,173 to Strum et al., issued for "Computer-Based Surgical Services Management System," describes a complex database running on a server and display system to coordinate surgical services at a medical center, but it is updated only periodically, not continuously. It also does not provide for remote notification and interaction by the medical center personnel.

In another aspect of the invention, in typical hospital settings such an operating room, ICU, recovery room etc., there are multiple medical devices surrounding a patient. For convenient, efficient assessment of the data collected and to control these devices, it is helpful to have their associated data displayed on a single monitor to have all the relevant information on a "single piece of glass". To achieve this, typically, a medical gateway (typically a general purpose PC computer) is setup to receive data from all the surrounding devices, convert the data to a standard format, synchronize it, and arrange for its display on a monitor proximate. But general purpose PCs, despite being commonplace, are actually an exceedingly varied and complex group of devices, each needing a specific setup and configuration, and ongoing maintenance of both software and hardware to maintain system security and efficiency. Simply put, the maintenance of general purpose PCs dedicated to data display ends up being a substantial expense for hospitals.

Biondi et al, U.S. Pat. No. 8,886,792B2, and Gao-Saari et al, U.S. Pat. No. 8,225,015B2, show the complexity and criticality of providing an integrated display from multiple heterogeneous medical devices in various circumstances, but provides no simple, stable, inexpensive solution for any specific hospital setting.

SUMMARY

In accordance with the present disclosure, embodiments of a system, method, and apparatus are described which eliminate or ameliorate the problems and disadvantages associated with previous systems, methods, and apparatuses.

Due to the exponential data availability from growing health-related devices, the risk of data not being collected, or worst, being wrongly associated, grows exponentially. In particular embodiments, the MDGS opposes this trend by using the same data to augment the data affinity and isolate and indicate possible association or data integrity errors.

When errors are detected from automated systems or from a later check or evidence, errors are propagated through related data, and when the data, a wrong association or time reference is corrected and signed with block-chain, the whole time segment of the data must be resent to the subsystem. Particular embodiments include the MDGS as the True and Complete Source of Data which should be used as the front end for subsystems.

By concentrating all available medical relevant data into a single source, and providing a subset of data to each receiving subsystem with the correct source and time reference, the Medical Data Governance System becomes the True Source of Data and guarantees the data consistency through the use of block chain signatures.

The instant invention provides a simple, stress-free, inexpensive connection and data-combining scheme requiring no special effort or consideration on the part of the medical personal attempting to care for patients in a wide range of hospital settings.

In another aspect of the invention, a system of servers is provided, which communicate data in real time with white boards stationed in the operating rooms of a healthcare facility. Medical personnel and healthcare facility staff members can view the formatted data on a white board and input new or revised data directly on the white board or at an input station near the white board.

Further in this embodiment, mobile phones carried by medical personnel and healthcare facility staff run applications enabling the real time display of data communicated by the servers and allowing the input of new or revised data into these mobile phones to be transmitted to the servers and displayed when appropriate on whiteboards and other displays throughout the facility. The mobile phone applications further permit the alerting of specific personnel, other mobile phone carriers and throughout the facility.

In another aspect of the invention, the problem of long-term reliable, secure connections to multiple heterogeneous medical devices and combining the displays of the data they produce for efficient apprehension is solved. The instant invention provides a simple, stress-free, inexpensive connection and data-combining scheme requiring no special effort or consideration on the part of the medical personnel attempting to care for patients in a wide range of hospital settings.

BRIEF DESCRIPTION OF THE DRAWINGS

For a more complete understanding of the present disclosure and its advantages, reference is now made to the following description taken in conjunction with the accompanying drawings, in which like reference numerals represent like parts.

FIG. 19 is an illustration of a stop light alert icon in an embodiment.

FIG. 20 is an illustration of a stop light alert icon in a small window on the desktop display of an administrator.

DETAILED DESCRIPTION

Figure 1:
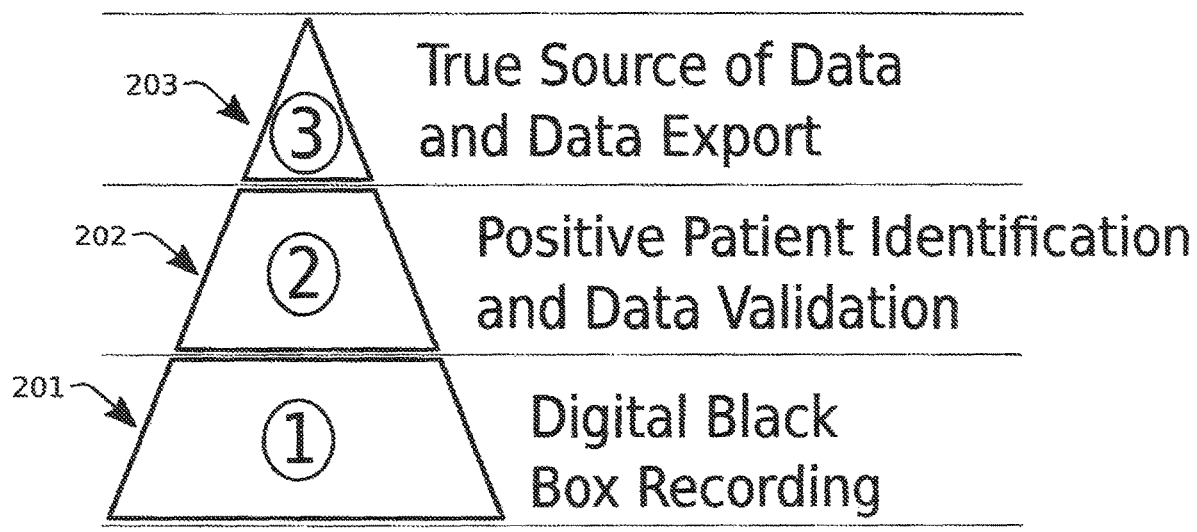
FIG. 1 is a block diagram overview of a Medical Data Governance system (MDGS) according to an embodiment of the invention.

FIG. 1 is a block diagram overview of the three functional layers of a Medical Data Governance System (MDGS) in an embodiment. The base layer 201 is digital black box recording of patient data. The middle layer 202 is positive patient identification and data validation. The top layer 203 is true source data and data export for research and other purposes.

Binding Location (geo-localization, indoor localization), Time, Provider, Patient is associated with data obtained from isolated or networked medical and medical relevant devices. The MDG collects data from medical devices, identifies them, normalizes and time synchronizes all the data outputs while storing them safely, with tamper detection methods (such as blockchain) local to the source of data. Partial and/or metadata about the collected data are used to identify the related patient, patient location, patient provider, source of data and location from whom the data had been collected when available. In the process described as MDG, the normalized data along with time, time span, location, patient are securely stored and saved for data export into third party systems (data consumers) or stored for later export. The process of binding Location, Time, Provider, Patient to the data can occur pre or post data collection, generating new dataset at each intervention or association, creating incremental dataset groups. For example, complete patient association can be done hours or days after the data had been collected, as well preset before the data is collected from the medical device.

Patient Treatment Time Optimization and Device Asset Management

MDG provides a true source of data that can highlight the schedule time variations of exams and other medical treatments and provides tools for the rescheduling feedbacks, contacting and receiving feedbacks from patients/physician/healthcare professionals thus introducing general system flexibility through the use of lean process and six sigma methods.

MDG leverages modern communication methods (phone apps, emails, web services . . . ) and easily links patient and physician/other healthcare professionals to the scheduled use of medical devices. After unexpected events that may cause a miss in scheduled operations, the MDG may create a backup schedule to preemptively fill the gaps and may facilitate healthcare and schedule professionals to optimize machine time usage. This could create a new marketplace for priority services for those patients that opt for it.

Patient/User Data Monetization by Patient/User, Institution or Combination Of

MDG enables patients/users and or Institutions to monetize their vitals, medical relevant, patient data collected during the stay inside the healthcare institution, as well through the extended data collected over period of time in a multiple stays or spot measurements in healthcare institutions. Patients could establish a relationship with a third party (such as drug manufacturer, independent drug trails projects, undisclosed trails to the institution) and provide to the third party normalized data collected, organized and provided by the MDG used by the healthcare institution, and provided to the patient in different standardized format, even in near real time. The institution might not be aware of the final user of the patient data. MDG can create additional revenue to the institution by charging such a service per patient and per data processed. MDG can track and trace data usage per patient and assets. MDG through the export of all specific, validated clinical data, medical relevant data, could create a new data-based economy.

Patient Notification and Pre or Post Consent of Data Use for Second Opinions, Medical Treatments, Specific Research, Validation, Education or Application.

MDG is solving the problem of giving consent and approval, or notification for use of the patient data for second opinion, medical treatments, specific research, validation project, educational purposes. Specific patient or user data is previously screened based on always updated, public, generic, anonymous metadata (for example: sex, age, days in hospital, normalised data content and length: heart rate, respiration rate, drugs . . . )).

MDG can handle patient consent using modern communication methods (phone apps, emails, web services . . . ) and provide patient consent for his data to be used in a specific research or validation project, with or without compensation. MDG can provide patient consent and access to the data to specific users, like doctors, physician, and other specific medical professionals. MDG can provide specific code associated to the data, that, based on necessity, can provide, if granted by the user or proxy consent, provide protected personal identification, family relations or other protected personal data.

Research Dataset Optimization

MDR allows for third party statistical analysis (research) on the whole population dataset, without exporting or providing data to the third party, but rather comparing the result to the legally available consent subset group. A statistically relevant result might indicate a minimal group of statistically significant subset of data to search consent and optimize the time for valid and repeatable dataset.

Data Normalization

Data normalization appears to be a key element for application of Artificial Intelligence in Healthcare. MDG, through the acquisition of higher frequency (sub-minute/sub-seconds), high fidelity data, patient identification, provider identification, data validation, time synchronization, localization of different, non-homogeneous clinical, medical relevant, patient relevant data from isolated, standalone medical devices or networked devices, can provide a superior, in terms of quality and quantity, subset of normalized data.

Metadata

MDG collects and stores all available data from any potentially source of data, localizes and time synchronizes all data points. Metadata such as, healthcare provider, environment temperature, hours of operation of medical device, time from last service, related errors can provide almost endless source of data for future use or research.

An Overall Solution to the Lack of Standards and Interoperability

MDG, as a sole purpose of true source of data, and without any specific end user purpose serves as a interoperability and standardization tool, enabling the health industry to leverage stored data through new and old standards based on the need.

Root-Cause Analysis and Quality Improvement Classification

As a most complete data gathering and presentation tool, any adverse case or event can be studied up to the maximum details reordered by the MDG. MDG tools helps retrieving patient identification, provider identification, data validation, time synchronization, localization of different, non-homogeneous clinical, medical, medical relevant, patient relevant data after adverse events, providing tools for analyzing risks, therefore introducing quality, process, outcome improvements. This classifies MDG as a quality improvement tools, therefore protected from legal perspective to be used as a proof of malpractice or errors.

Non-medical user notification and pre or post consent of data use for specific research, validation, education, marketing or application. The ability of handling critical data can be extended to several personal user data in different fields outside of medical.

MDG solves the problem of giving consent and approval, or notification for use of the user data for specific research, validation project, educational purposes, marketing or application. Specific user data is previously screened based on always updated, public, generic, anonymous metadata (for example: sex, age, days in hospital, normalised data content and length). MDG can handle user consent using modern communication methods (phone apps, emails, web services . . . ) and provide user consent for his data to be used in a specific research or validation project, with or without compensation.

Figure 2:
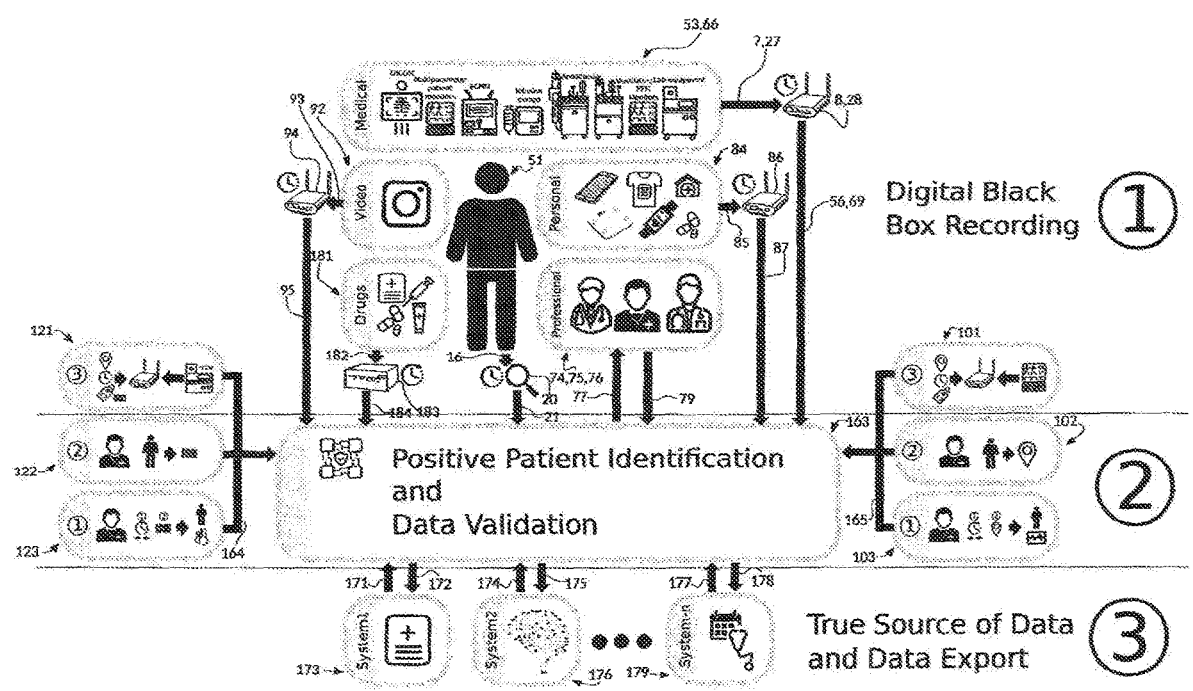
FIG. 2 is an illustration providing high-level detail about each layer of the MDGS pyramid of FIG. 1.

FIG. 2 is an illustration of a simplified 3-layer MDGS in an embodiment. Artificial Intelligence and Machine Learning systems require a medical data governance middleware to assure proper, normalized and verified data inputs. Legacy health information systems and electronical medical records were designed to receive only a portion of the exponentially increasing data medical devices can create and can be collected. Also, outdated HIS/EMR (Healthcare Information Systems/Electronic Medical Record) and inadequate patient identification and association can cause a serious bottleneck for data-hungry personalized medicine, real time applications, and in practice, most medical device data are not recorded at all.

Layer (1): Black Box Recording

Hospital medical devices, continuous monitoring systems and laboratory devices 53, 66, through the use of proper physical and software drivers 7, 27 are collected by Medical Device Data System (MDDS) devices 8, 28 and location/time synchronized, optionally signed with block chain service, and made available to the second layer of the MDGS—Positive Patient Identification and Data Validation.

Similar to laboratory devices, video 92 can be transferred 93, recorded 94, location/time synchronized, and then transferred when convenient 95 to a central repository and patient locked by the second layer. Wearables and home or community care data and sensors 84, generally available through BLE (Blue Tooth Low Energy, BT4.1) wireless protocol 85, can be registered and time synchronized by portable MDDS device or phone application 86, and available or optionally transferred 87 when possible to a central repository.

Professional notes, comments, orders and communications, generally known as Journaling, 74, 76 can be tracked, reported and stored 77, 79 via third party systems and solutions.

Drug Distribution, Administration and all other third party software and systems 181, 182, 183 can be tracked, tagged, stored, time synchronized and made available 184 to the second layer.

Each MDDS has a location 101 and metadata configuration panel available for setup 121 so the medical device data can be location or patient tagged for patient data association and data validation.

Layer (2): Positive Patient Identification (PPI) and Data Validation (DV)

As described below in more detail in the description of FIG. 5, PPI and DV depends on previous location and metadata setup of MDDS 121, 101 (FIG. 2) and proper data entry of metadata 122 or location 102, and active healthcare professional confirmation of patient location time presence 103 or the proper patient identification process 123. Upon PPI and DV, different segments of Digital Black Box recordings are patient and time segment tagged 163 and available to the third layer, True Source of Data and Data Export.

Layer (3): True Source of Data and Data Export

By concentrating all available medical relevant data into a single source, and providing a subset of data to each receiving sub-system 173, 176, 179 with the correct source and time reference, the Medical Data Governance System becomes the True Source of Data and guarantees the data consistency through the use of block chain signatures.

Due to the exponential data availability from growing health-related devices, the risk of data not being collected, or worst, being wrongly associated, grows exponentially. The MDGS opposes this trend by using the same data to augment the data affinity and isolate and indicate possible association or data integrity errors.

The MDGS, as the True and Complete Source of Data, should be used as the front end for sub-systems. When errors are detected from automated systems or from a later check or evidence, errors are propagated through related data, and when the data, a wrong association or time reference is corrected and signed with block-chain, the whole time segment of the data must be resent to the sub-system rather than those subsystems being corrected independently.

Each medical subsystem 173, 176, 179 is designed to receive specific data with a specific frequency, quantity and quality. Sometimes the specific data, frequency, quantity and quality do not overlap between subsystems. From the Complete True Source of Data, the specific export drivers 171, 172, 174, 175, 177, 178 collect, filter, consistency check, transform and deliver appropriate data to each subsystem.

Figure 3:
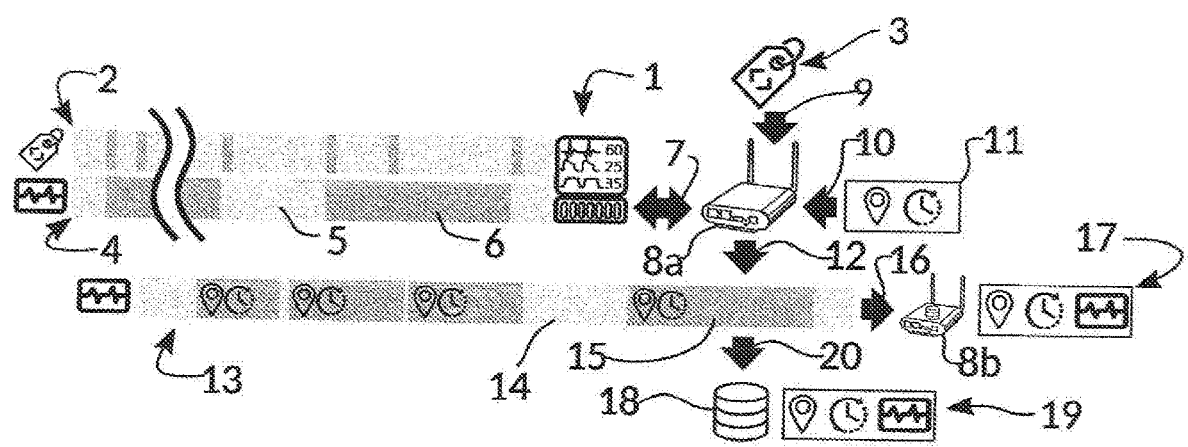
FIG. 3 is an illustration of the details of continuous patient monitoring measurement, part of the first layer of MDGS, Digital Black Box Recording, in an embodiment.

FIG. 3 is a block diagram illustrating details of one component of Layer (1) Digital Black Box Recording, in particular, the medical devices that measure continuous patient data, such as Multiparametric Patient Monitoring, Anesthesia machines, EEG and similar belonging to the "continuous" group of potentially retrievable medical data 4, where the session beginning, duration and therefore, its end can be associated using continuous, complete data flow without data interruption 6. Previous idle, non-patient data that is irrelevant and does not provide any information, except the fact that at that time patient data was not being collected is noted 5. Metadata such as device not ready, cable disconnected, device powered off is recorded 2, including but not limited to room temperature and pressure, video, and other environment data if and when available such as other medical devices connected 3 that provide essential information about the start and stop of the data valid session 6. Medical devices 1 usually have one or more data export mechanism 7 which is used from a Medical Device Data Systems (MDDS) 8a to extract and collect ALL possible data, along with metadata 2, 3 from specific software and hardware drivers and interfaces 9 and along with previously associated 10 location, metadata and clocktime 11 reference.

The MDDS stores 16 location sessions 15 with all medical data collected, metadata, timestamps and location identifiers 13 and keeps it for a limited time, for example up to 24 hours, before it copies it 20 to a centralized repository 18. Empty, non-relevant data 14 are simply not propagated and ignored.

The MDDS 8b can serve a complete time synchronized and location subset of near real time data 17 without intermediary subsystem, or if the complete dataset had been copied to a centralized repository 18, the past data subset 19 can be retrieved from the repository services 18.

Figure 4:
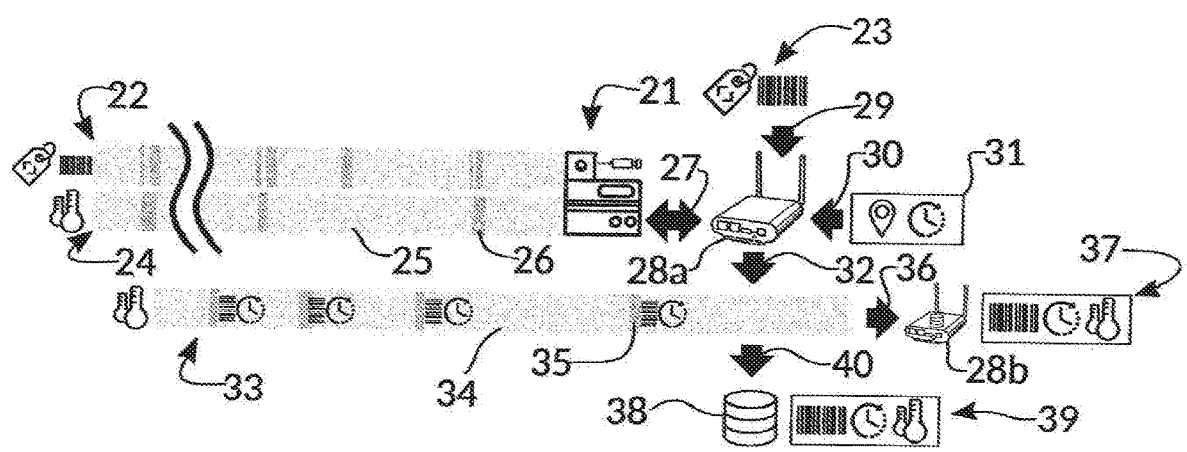
FIG. 4 is an illustration of the details of the recording of sporadic patient related data, part of the first layer of a MDGS, Digital Black Box Recording, in an embodiment.

FIG. 4 is a block diagram illustrating details of another component of Layer (1) Digital Black Box Recording, in particular, medical devices that measure sporadic patient related data 21 such as Blood Gas Laboratory Machines, Generic Laboratory Devices, Portable Non Invasive Blood Pressure devices, Scales and similar belonging to the "spot" group of potentially retrievable medical data 24. The session beginning, duration and result can be directly associated from meta-data, such as bar code patient ID, Point Of Care (POC) input, and the result 26. Previous idle, non-patient data that is irrelevant and does not provide any information is not propagated, except for the metadata indicating that at that time patient data results were not being collected 25. Metadata is included such as, but not limited to, Patient Bar Code ID, POC input, device not ready, cable disconnected, device powered off 2, but also room temperature and pressure, video, and other environment data such as other medical devices connected 3 that provide essential information about the start and end of the result data 26. Medical devices and Laboratory devices 21 usually have one or more data export mechanism 27 which is used from a Medical Device Data Systems (MDDS) 28a to extract and collect ALL possible data, along with Metadata 22, 23 from specific software and hardware drivers and interfaces 29 and along with previously associated 30 location, metadata and clock-time reference 31.

The MDDS stores 36 location sessions 35 with all medical data collected, metadata, timestamps and location identifiers 33 and keeps it for a limited time, for example up to 24 hours, before it copies it 40 to a centralized repository 38. Empty, non-relevant data 34 are simply not propagated and are ignored.

The MDDS can serve a complete time synchronized and location subset of near real time data 37 without intermediary subsystem, or if the complete dataset had been copied to a centralized repository 38, the past data 39 subset can be retrieved from that repository service 38.

In any case, the Layer (1) Digital Black Box Recording does not have Protected Health Information (PHI), and if it is provided, it is stripped off and eliminated from the stored data. The possible PHI is removed from drivers handling specific medical devices.

Block Chain Signature Anti Tampering Protection

Figure 5:
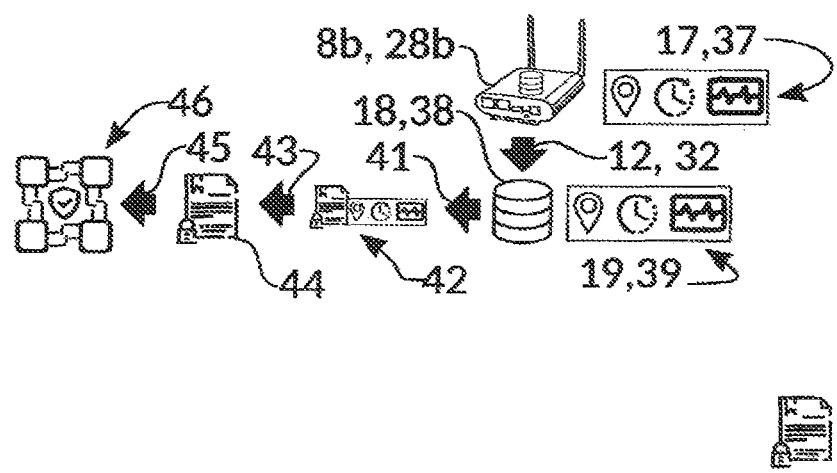
FIG. 5 is an illustration of the details of providing block chain signatures for black box recorded patient data sets in an embodiment.

When the MDDS 8b, 28b transfers the complete time synchronized and location data set 17, 37 to a centralized repository 18, 38, then as depicted in FIG. 5, the past data set 19, 39 is "signed" 41, 42, and the Signature 44 is produced 43. The signature can be transferred 45 or stored to the external Block Chain Server Authority 46 to tamper proof the data collected and have an external safety check for data consistency.

Electronic Black Box Recording Data Diagrams for Various Medical Data and Medical Relevant Data Sources.

Figure 6:
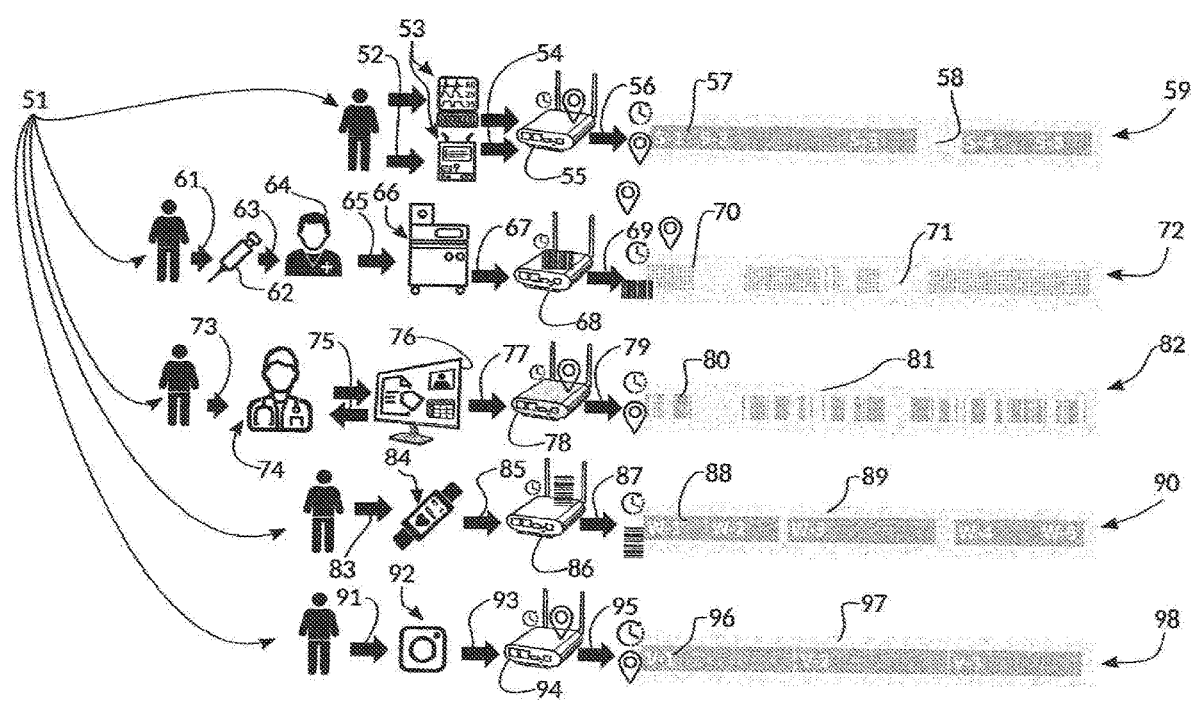
FIG. 6 is an illustration of the details of black box recording of a variety of different types of patient data in an embodiment.

Different medical and medical relevant data types are recorded, including location and patient ID metadata, and time synchronized with medical device data as depicted in FIG. 6. Continuous medical devices 59, laboratory devices 72, professional journaling and comments 82, personal wearables and fitness trackers 90, and video capture systems 98 store the non PHI (Protected Healthcare Information) only.

Continuous Medical Measurments 59:

When patients 51 are connected with physical sensors and leads 52 to medical devices 53 that have the capability to export real or near real time data 54 to an MDDS 55, the MDDS 55 will timestamp, location and metadata associate the data created 56 with a Digital Black Box Recorder dataset 59 consisting of different data sessions 57 and idle time 58.

Laboratory Data 72

Samples of blood or other patient relevant organic samples 61 are taken and temporary conserved 62 and transported 63 by healthcare professionals 64 then properly processed and electronically identified 65 by laboratory device 66. The lab equipment should have the ability to export metadata such as POC or ID-collected and lab results in an electronic format 67 which is collected and processed by the MDDS 68. The MDDS will timestamp, location, ID and metadata associate the data creating 69 a Digital Black Box Recorder dataset 72 consisting of different laboratory results 70, metadata of patient identification codes and idle time 71. Protected Healthcare Information is stripped off and assure the data to be deidentified matching a single universal identification code to be stored instead if not already provided.

Medical Journaling 82

Every patient 51 consult, visit or opinion 73 between patient 51 and the medical professional 74 can be recorded or have notes taken 75 by third party software or systems 76 and directly exported or queried 77 from the MDDS 78 systems at the place of creation (near the patient current location). The MDDS will timestamp, location, ID and metadata associate the data, creating 79 a Digital Black Box Recorder dataset 82 consisting of various notes and documents, video and audio notes 80, metadata of patient identification codes and idle time 81. Protected Healthcare Information will be stripped off and assure the data is deidentified matching a single universal identification code to be stored instead.

Wearables and Fitness Trackers 90

Patient 51 might have 83 various personal wearable devices operating with BLE (blue tooth low energy or similar technologies) 84 that can be periodically or constantly in communication 85 with a fixed or portable MDDS or personal phone MDDS app 86 that has been preprogramed with a BLE MAC address to receive and associate the medical devices with the patient. Like the continuous medical measuring 59 and the measure-result laboratory systems 72, data sessions are defined 87 with metadata such as MAC, location and the receiving MDDS ID 88 and not-relevant data segments 89.

Video and Medical Relevant Data 98

All patient 51 relevant video or medical relevant ambiental data 92 can be recorded 93, time and location synchronized by the MDDS 94 system. The MDDS will timestamp, location and metadata associate the video and/or ambient data creating 95 a Digital Black Box Recorder video or ambient dataset 98 consisting of different data session 96 and idle time 97.

Figure 7:
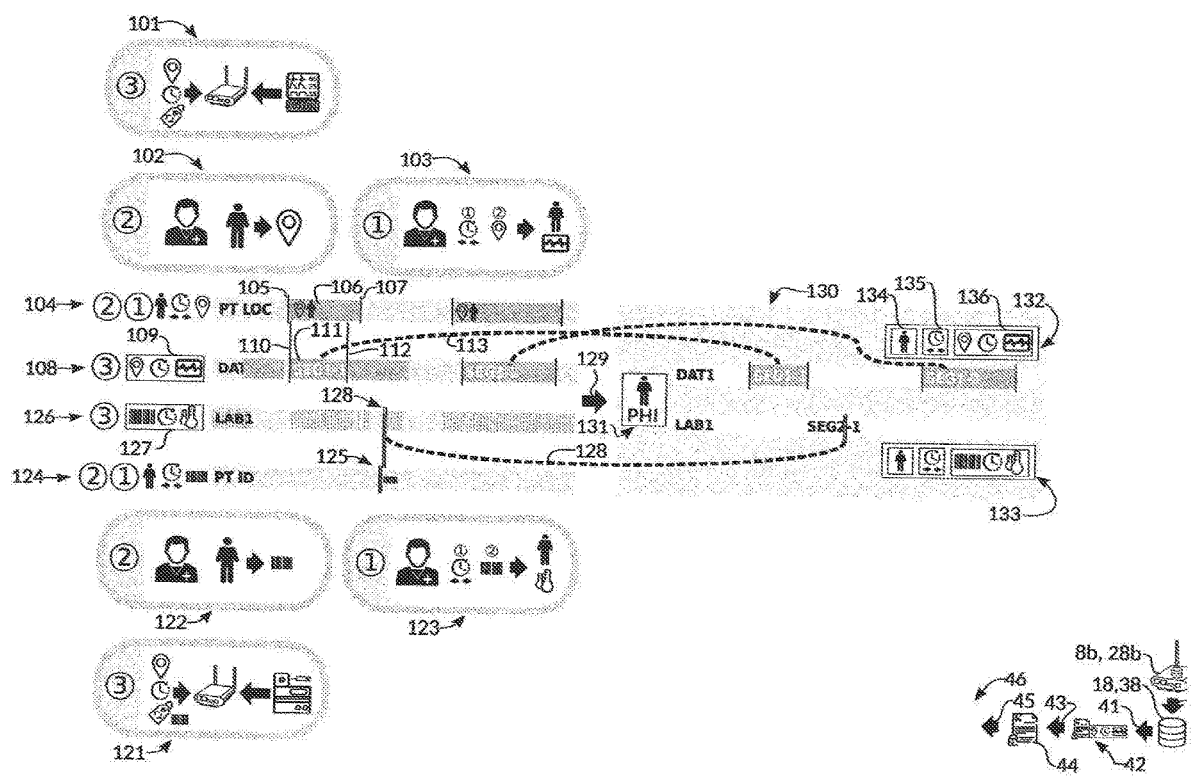
FIG. 7 is an illustration of the details of the second layer of a MDGS, Positive Patient Identification and Data Verification in an embodiment.

Second Layer of Medical Data Governance: Positive Patient Identification and Data Validation FIG. 7 shows the process of association between the patient and the data collected, or to be collected 101, 121. An external process, software or system, associates a Patient Identification code to a location 102 or patient-to-patient Identification code 122. An active healthcare professional, or someone that has been assigned to verify the patient data, patient location or patient identification, confirms the three key elements of the patient data triplets: patient identification and its code 134, segment or segments of time the patient was on location 135, and patient data collected at that location 109, 136 throughout the active process 103, 123.

Due to patient location recorded or provided by third party systems 102, 104 and data and metadata collected 101, 108, a subsession defined by start 105 and stop time 107, identified by a healthcare professional 106 or by third-party systems allows the precise selection of the appropriate and consistent data session 111 and seamlessly finetunes the accurate start 110 and stop 112 of the particular data session 113, then creates the building block of triplets 132 that constitutes a complete positive patient identification and data validation record 130.

For a laboratory, or multi patient systems such as laboratory machines, an action that immediately precedes or clearly relates to the result being consecutively transferred and collected by the MDDS system 121, a previously created Patient Identification code 122 is collected as metadata and time synchronized with the result that is collected. An active process of confirming the data 128, patient and patient id 125, and validity of test result 123 creates the triplets 133 from the data set recorded 126 and the patient, time segment and location information 124.

Protected Healthcare Information and Anti Tampering with Block Chain Signature

Figure 8:
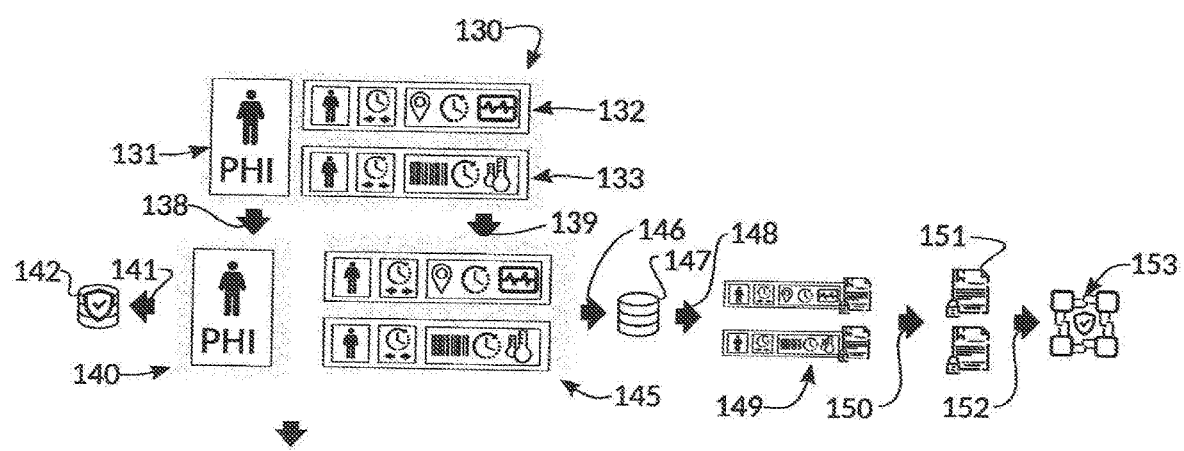
FIG. 8 is an illustration of the details of the process of storing Protected Healthcare Information (PHI) and providing a PHI data set with a block chain signature.

As depicted in FIG. 8, the process of active Positive Patient Identification and Data Validation creates multiple patient time segment data records 132, 133 associated with the patient 130 where PHI is shown, visible 131 and essential for positive patient association and the data validation process. After the modification of the previous data segments due to different information such as different times or location association, or upon creation of new triplets, they are stored 139 separately 145 from the storing 138 of the PHI 131. PHI 131 is stored 138 on third party systems 140, 141 running on a protected database system 142.

Upon confirmation of the triplet's association 145, each triplet is recorded 146 on a database 147 that triggers an automatic digital signature of each record 149 and a signature certificate is transferred 150, 151 and delivered 152 to the third party Block Chain system 153 for safety and anti-tamper proofing of the data.

Medical Data Outputs and Deidentified Research Data Exports

Figure 9:
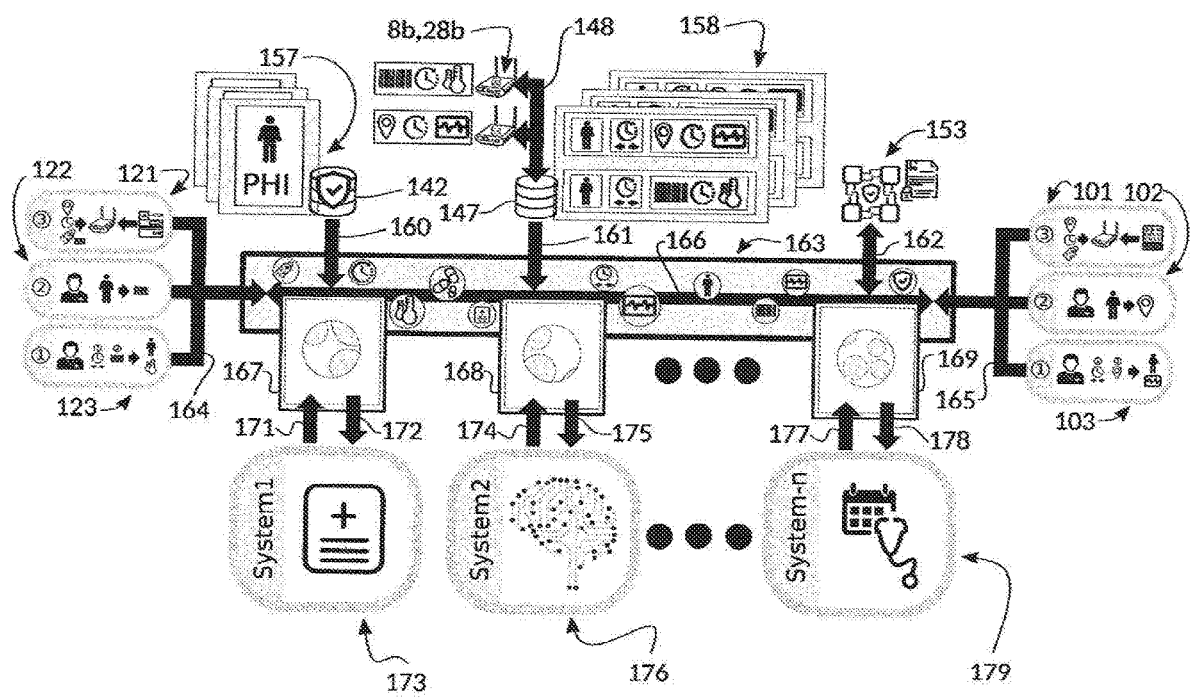
FIG. 9 is an illustration of the details of the third layer of a MDGS, data extraction and export, in an embodiment.

The third layer of the Medical Data Governance System is data extraction and single point of truth for legacy and future healthcare data systems. As depicted in FIG. 9, dependencies for adequate data outputs are defined as follows: the database 147 is populated with multiple 158 patient associated data session records 145, and the different PHI data 157 are also recorded and protected from non-authorized use 142 and interfaced to the MDGS 160. A Block Chain external service 153 is used to prevent data tampering and interfaced to the MDGS 162. Real time data is available through secure proxy tunnel 148 from bedside MDDS systems 8b, 28b. Previous location and proper time reference, metadata drivers and medical device drivers are set and ready 101. Drivers for barcode or POC inputs are properly installed to the MDDS system 8b, 28b, connected to laboratory, spot-like, multi patient medical systems 121.

Patient ID is coded to barcode or POC patient code from third party systems and is available for research 122. Patient locations are available from third party systems or documented 102. Active healthcare professional(s) or an adequate automated system is assigned to verify and confirm patient id, location or barcode ID, time span, and to validate the collected data 123, 103.

True Source of Data and Data Export

As depicted in FIG. 9, by concentrating all available medical relevant data into a single source designed to handle very large, different data formats (data, metadata, values, trending, waveforms, video etc.) and providing a subset of data to each receiving subsystem 173, 176, 179 with the correct source and time reference, the Medical Data Governance System becomes the True Source of Data and guarantees the data consistency through the use of block chain signatures.

Due to the exponential data availability from growing health related devices, the risk of data not being collected, or worst being wrongly associated grows exponentially. The Medical Data Governance System opposes this trend by using the same data to augment the data affinity and isolate and indicate a possible association or data integrity errors.

An MDGS 163 data export subsystem with specific, recorded and real time data in relation to location or to patient source can be configured 167, 168, 169 for output system 173, 176, 179. Internal to a MDGS export data sub-item, a backbone of all data is available 166 for export drivers 167, 168, 169 access. For example, a minute-based representative value subset for a patient can be configured (exported to EMR, along with the triplets Unique Identifiers (IUD) for later more in-depth review 173, 176, 179 through a different export driver. Selected high frequency, high accuracy data can be exported, after a prolonged period like 30 or 60 days, to AI systems for machine learning processes 173, 176, 179.

In essence, data export of the same complete data acquired from medical devices 167, 168, 169 can be different depending on the different requirements of exporting systems, and the export drivers and protocols 171, 172, 174, 175, 177, 178 can be created on demand from original, complete, high frequency, high fidelity, rich data sets stored in Digital Black Box records, time synchronized and with positive patient identification and data validation.

In another aspect of the invention, hospitals and other healthcare facilities providing surgical services must coordinate a myriad of resources, medical personnel, and hospital staff to provide optimum and efficient care to their patients. Information about status of these resources and the facilities' patients must be updated constantly and be available to the relevant medical personnel and facility staff in the operating rooms (ORs) where the surgical services are delivered, in other ancillary rooms of the facility, and to medical personnel and facility staff who may be in remote locations.

Figure 10:
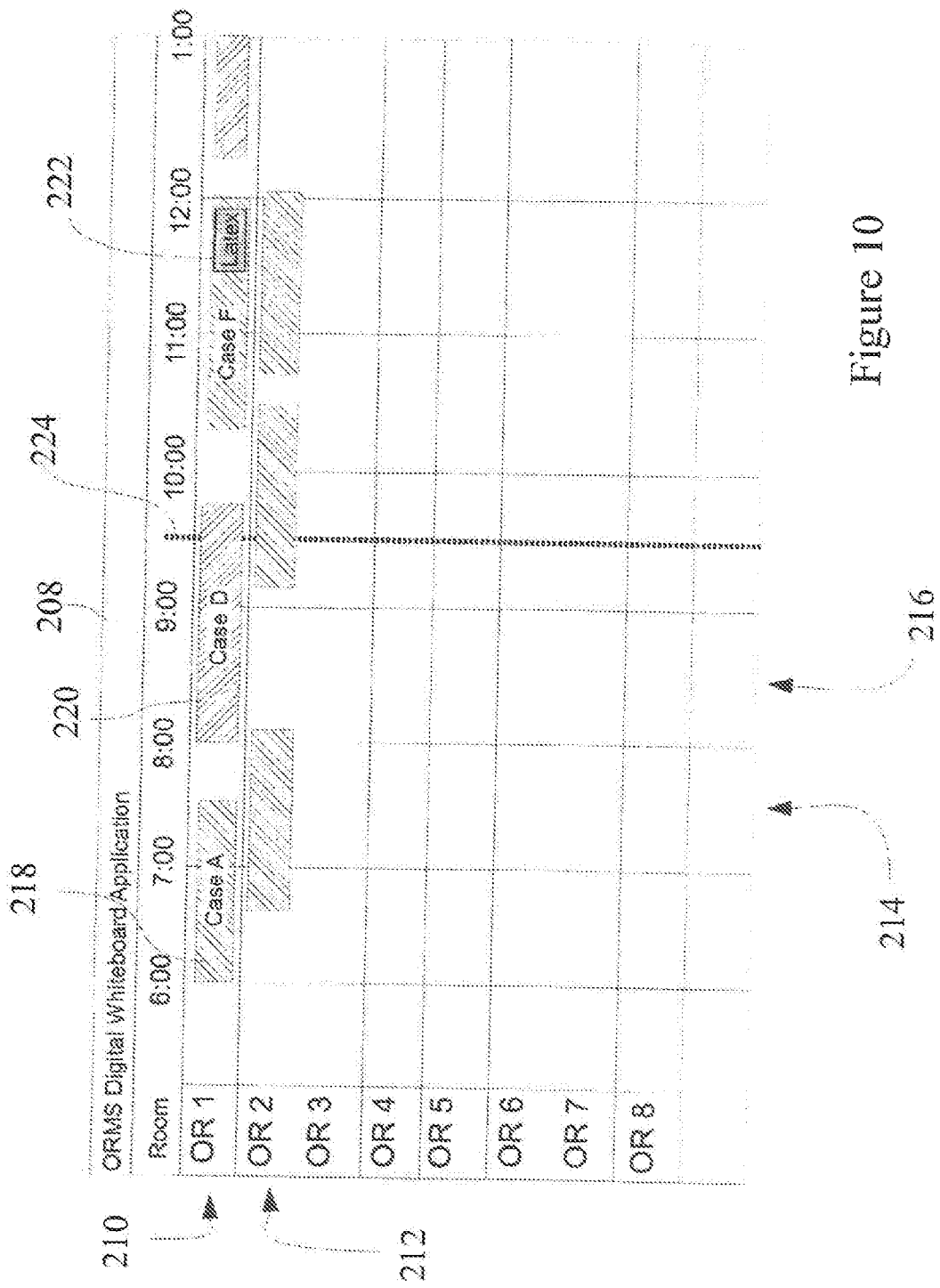
FIG. 10 is an illustration of a hospital daily schedule display on an operating room digital white board.

In an embodiment of the invention, FIG. 10 is an example illustration of a daily schedule 208 for the operating rooms of a hospital or healthcare facility. Schedule 208 would be displayed on a multiplicity of digital whiteboards in various places of the healthcare facility such as the anterooms of the operating rooms. The rows of schedule 208 correspond to different operating rooms of the facility. For example, rows 210 and 212 correspond to OR 1 and OR 2 respectively as indicated. The columns, for example 214 and 216, correspond to the time of use of the operating rooms by the patient cases undertaken. The current time of day is indicated by a vertical line 224 through schedule 208.

The patient cases scheduled are depicted as shaded or colored blocks, for example 218 and 220, extending for the length of time they will occupy the operating room. Text within the blocks, such as shown 218 and 220, provide details of the cases such as the name of the patient and the procedure planned. The type of shading or different colors of the blocks 218 and 220 indicate the case status and current location of the patient. Alerts concerning the case such as pertinent allergies may also be indicated by a separate shaded or colored area with a case block as illustrated at 222 for example. Such a color-coded, resource-focused schedule in combination with a display of simplified information is unique in the setting of a hospital or health-care facility and is surprisingly effective in providing a comprehensive picture of the data needed to optimally organize the doctors, nurses and other health care personnel, and the resources they need, and further, uniquely and surprisingly enhances the making of quick, accurate decisions in critical situations.

Figure 11:
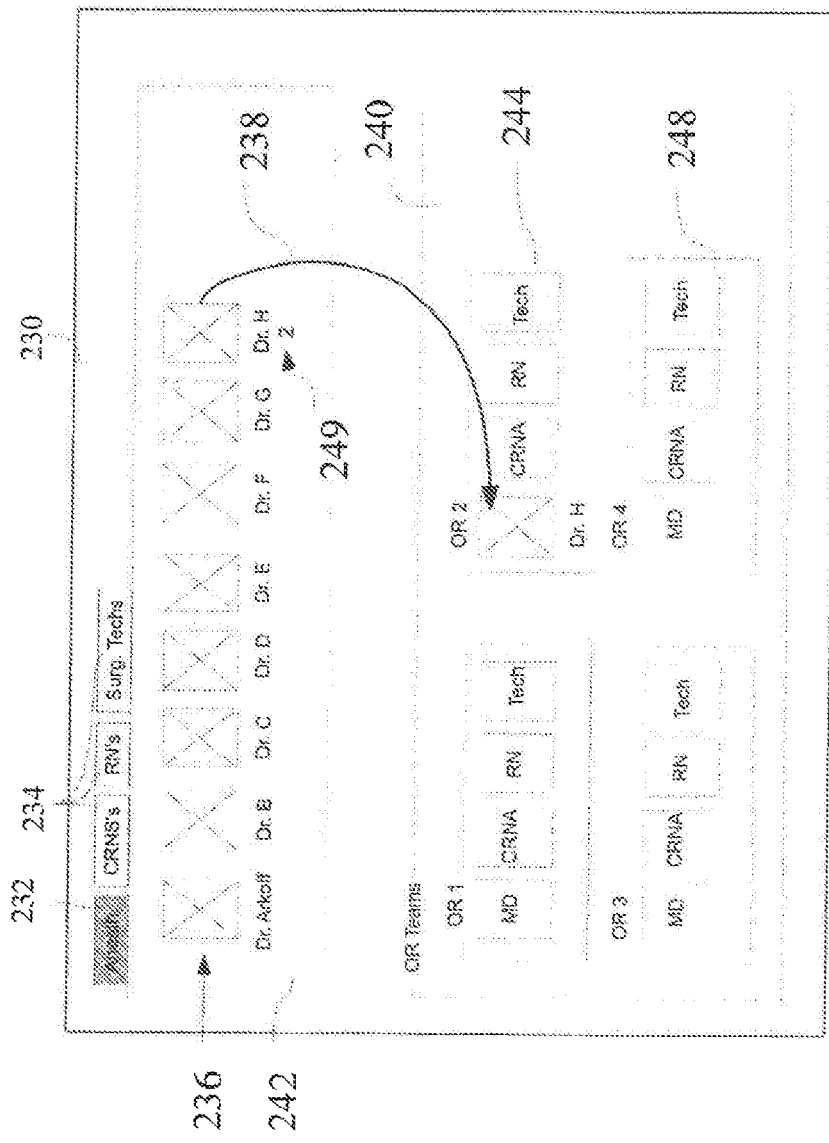
FIG. 11 is an illustration of the team building display on an operating room digital whiteboard in an embodiment of the invention.

Surgical teams can be formed and assigned easily using a display 230 of individual health care facility personnel organized by specialty and work shifts such as illustrated in FIG. 11. Medical personnel by specialty are shown at the display top 242. In this example, the group of anesthesiologists have been selected to be displayed by highlighting tab 232. Once selected, the anesthesiologist's names and pictures are displayed in a row as indicated 236. Alternatively, if any of tabs 234 were selected and thus highlighted, the corresponding group of medical personnel would be displayed at the top 242.

To form a particular team, individual personnel available to work that day are dragged and dropped to the appropriate position in the chosen team in lower box 240. As an example, in FIG. 11, Dr. H has been dragged and dropped on the MD position on OR 2 (numbered 244) as indicated by arrow 238. In some instances, personnel can be assigned to more than one teams. In such a case, the picture and name of the person remains in the top row until he has been assigned the maximum number of times. This is shown by example with the photo of Dr. H remaining in the top row 236 at the same time his photo is displayed as a part of OR 2 (numbered 244). The maximum number of times a person can be assigned to a team is typically determined on an individual basis.

Once formed, the teams are dragged and dropped on particular patient cases and then displayed on the main schedule 208 on whiteboards and other displays throughout the facility. The dragging and dropping process can be carried out directly on the whiteboard or other display using a method of digital input such as computer mouse or stylus, or to facilitate quick and easy input to the display on a digital whiteboard, a user can use for example a tablet computer communicating with the whiteboard via a bluetooth or other wireless connection and displaying a facsimile of the team building screen.

A suitable digital whiteboard capable of displaying the schedule 208 is the Hitachi Starboard FXTRIO Interactive Whiteboard available from Hitachi Solutions America, Ltd., 601 Gateway Blvd. Suite 100, South San Francisco, Calif., although many other digital whiteboards or other computer-controlled display systems can be used. If the Starboard FXTRIO digital whiteboard is used, then a software interface such StarBoard Software also available from Hitachi Solutions can be used to facilitate the creation and modifications of schedule 208.

Figure 12:
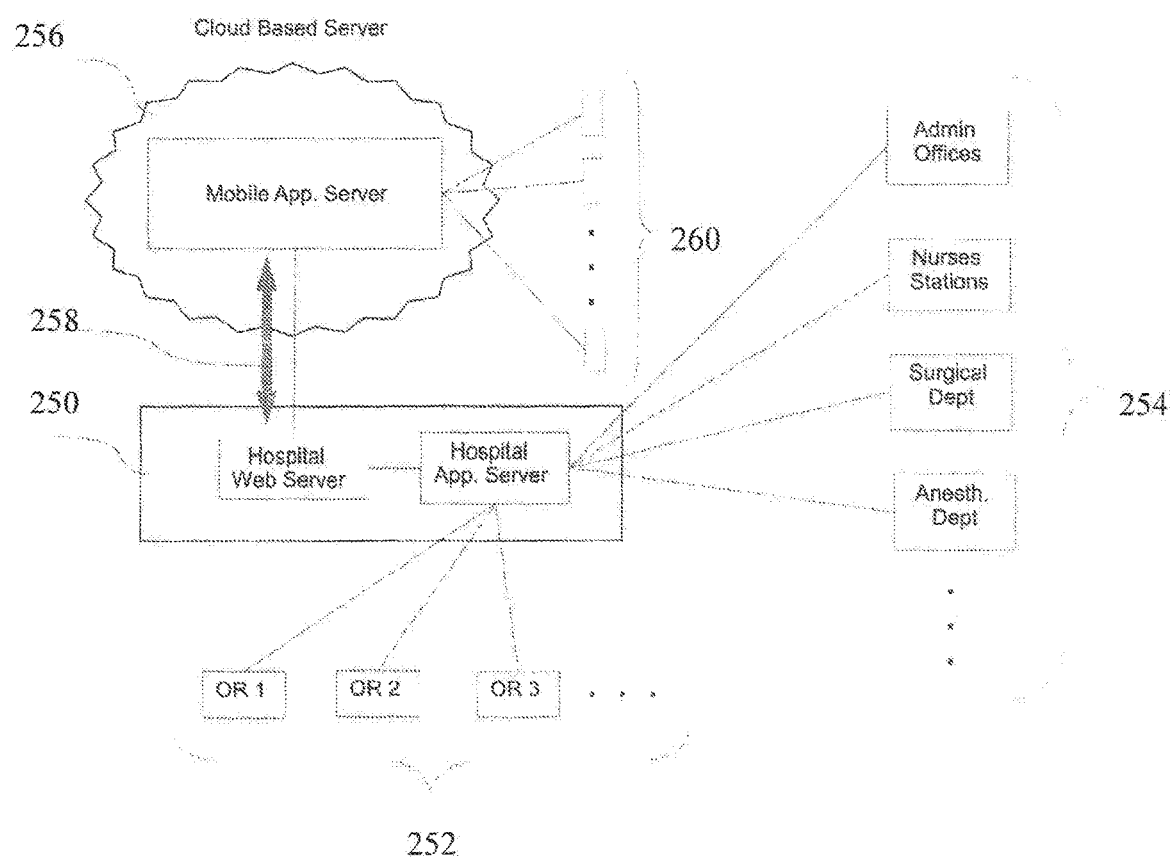
FIG. 12 is a block diagram detailing the arrangement of specific servers in an embodiment.

FIG. 12 is a block diagram overview of the overall system running the ORMS software in an embodiment. Local server 250 receives, stores, calculates, and transmits data in forms such as schedule 208 to the facility operating room sites 252 and facility offices and stations 254. Schedule 208 and other data may be displayed on for example digital whiteboards, desktop displays, tablet computers, or mobile devices depending on the needs of the site or office. The local server 250 is in continual, real time communication with cloud-based server 256 which is not physically located at the healthcare facility. In an alternative embodiment, all variable patient, case and resource data is maintained on the local and cloud-based servers and downloaded to the individual whiteboards, displays, stations, or departments, but calculation and formatting of the schedule and determination of alerts is done by applications or software modules running on the PC's or embedded computers associated with each individual whiteboard, display, station, or department.

All substantive data on local server 250 is continually backed up on cloud-based server 256 and vice versa as indicated by arrow 258. In this embodiment, the data continually backed up includes all current information about the patient cases the hospital has undertaken and the information about the health care facility resources and personnel necessary to calculate and display the schedule.

Cloud-based server 256 transmits a facsimile of the schedule 208 and other data to apps on the mobile phones 260 of doctors and other relevant health care personnel. Also, via this path, alerts can be texted or otherwise transmitted to specific personnel. An alert is short message or datum of high importance and urgency. Alerts may for example indicate an unexpected problem or delay with a particular patient or case, or patient overcrowding at a particular stage or location within the facility. Alerts can be manually triggered for example by personnel at any of the offices and stations 254, or automatically triggered by one of the servers based on calculations from data input by personnel at for example operating room sites 252 or offices and stations 254. Such automatically triggered alerts can be fixed as a part of the system design or can be customized by various healthcare facility personnel.

An alert displayed on one or more mobiles phone 260 can be responded to immediately by a user or users and data in the response displayed in real time on one or more of the digital white boards near the OR's 252, station or office desktop displays 254 or other displays in the healthcare facility or in the overall system. The response can be a direct change in the displayed schedule or used to automatically calculate a change in the schedule which is then displayed. Personnel at these sites can then make further adjustments to the schedule or input other data accordingly. Correspondingly, any changes in the schedule such as illustrated FIG. 10 will be transmitted in real time to the other sites and the apps on the mobile phones 260. Having the capability of alerts for mobile users which can be responded to by transmitting schedule changes to the overall system is a unique and surprisingly effective method of optimizing the resource usage of the hospital or health-care facility.

Local server 250 can be implemented using a standard PC with for example an Intel Ivy Bridge microprocessor running the Windows 7 operating system. Of course Apple or UNIX-based computers, among others, could also be used as would be obvious to engineers with ordinary skill in the art. Cloud-based server 256 can be implemented for example using a commercial cloud computing service such as Amazon Web Services available at URL http://aws.amazon.com/ or using standard PCs at a remote location. Software development for the servers and the station or desktop modules can be done in Visual Basic with the Microsoft Visual Studio development environment although myriad other programming languages and development environments can be used. The displays such as illustrated in FIGS. 10 and 11 are typically implemented using an internet browser such as Firefox and coded in HTML although other browsers or direct implementation in Visual Basic or many other programming languages and development environments known to software engineers with ordinary skill in the art can be used.

Figure 13:
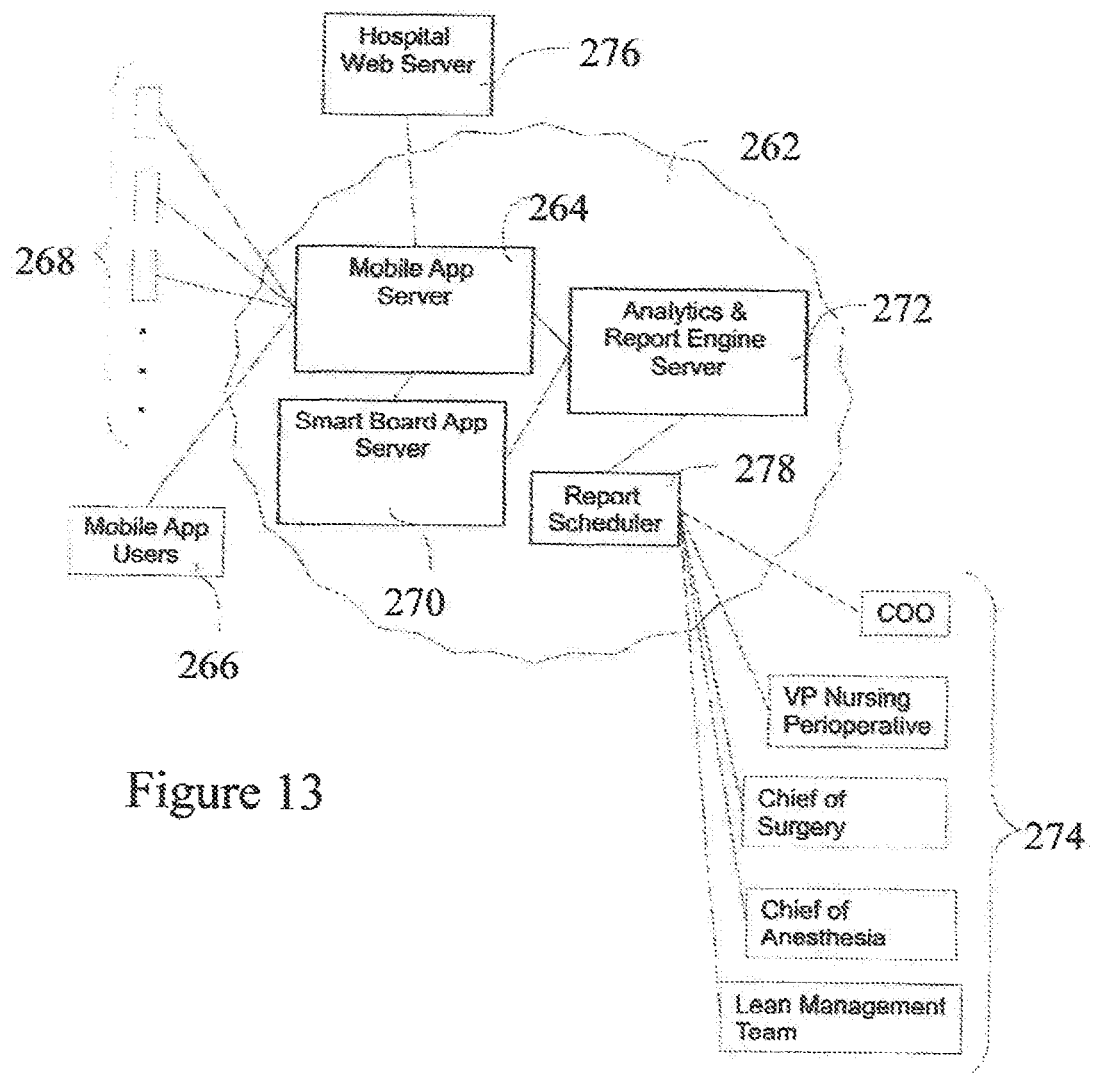
FIG. 13 is a block diagram illustrating the arrangement of specific servers within the cloud server in another embodiment of the invention.

FIG. 13 is a block diagram of an arrangement of application-specific servers at remote cloud server 262 in another embodiment of the invention. In this embodiment, cloud server 262 includes a mobile applications server 264 which communicates directly with the mobile phones of users running an app 266. The mobile applications server can also send and receive SMS text messages to the mobile phones 268 of users whose phones do not have the mobile app capability.

Cloud server 262 also runs the digital white board application server 270. Both the digital white board server 270 and the mobile applications server 264 communicate data directly to the analytics and report engine server 272 which analyzes said data and creates appropriate reports. Said reports are sent periodically via the report scheduler 278 to the appropriate personnel, collectively 274, at the hospital. Generally, realtime data is communicated to and from the hospital display locations, stations, departments, and offices via the hospital web server 276.

Figure 14:
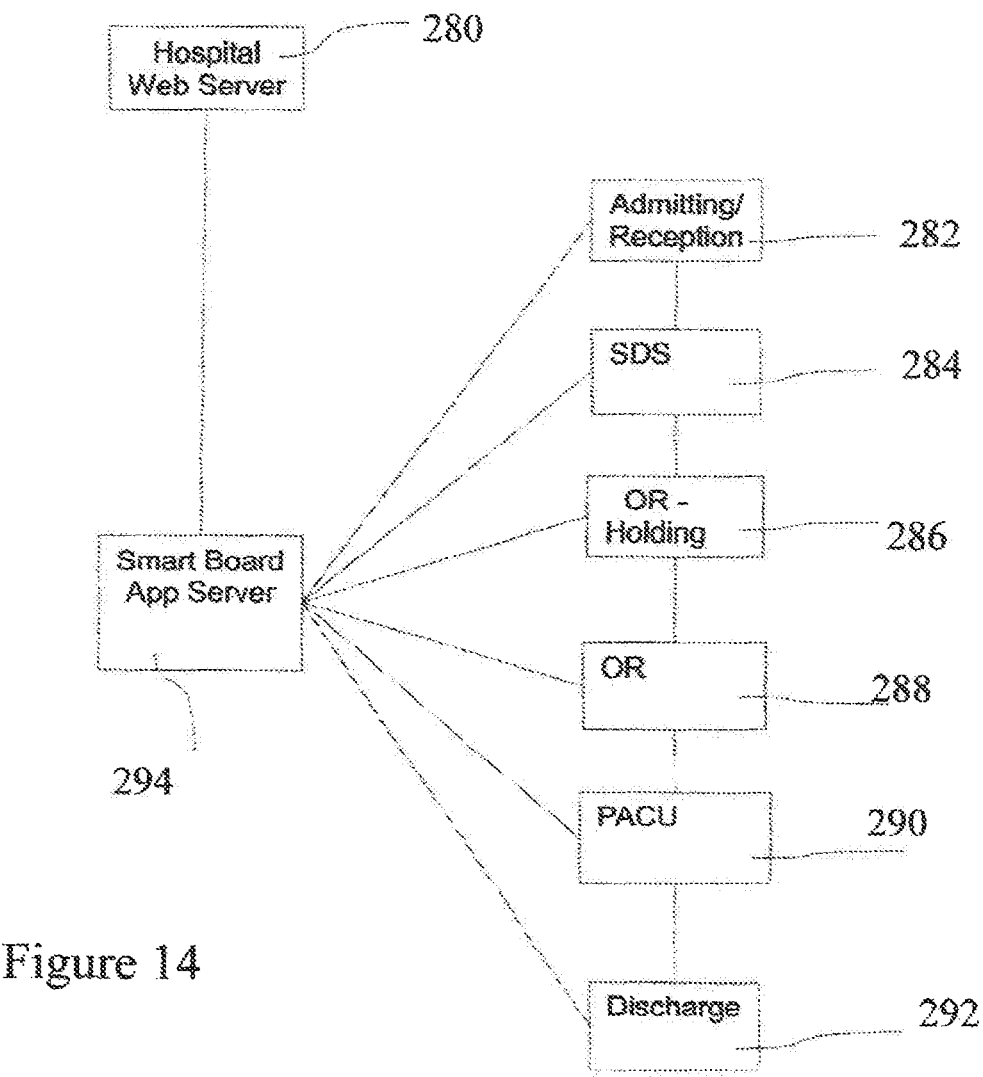
FIG. 14 is a block diagram illustration of patient movement through the hospital and corresponding data entry.

FIG. 14 is a block diagram showing patient movement through the health-care facility. In this embodiment, when a patient enters the reception area 282, his arrival is input to the hospital web server 280 by admitting personnel and his case is displayed on the OR schedule such as illustrated 218 and 220 for example on FIG. 10. As the time for the patient's operation approaches, he moves to SDS 284 and then to the OR holding area 286.

At each department or station, the patient's progress is updated on the OR schedule by the staffing personnel who typically input the data using desktop PCs or tablet computers. The ORMS software module running on the desktops PCs or tablet computers is typically customized for each department or station.

At the appropriate time and when the surgical team and all resources are ready, the patient moves to the OR 288 and the operation is performed by the surgical team. After the operation is complete, the patient moves to the PACU 290 and when ready the discharge area 292 where the patient may fill out a survey which he inputs directly to the hospital web server 280.

Figure 15:
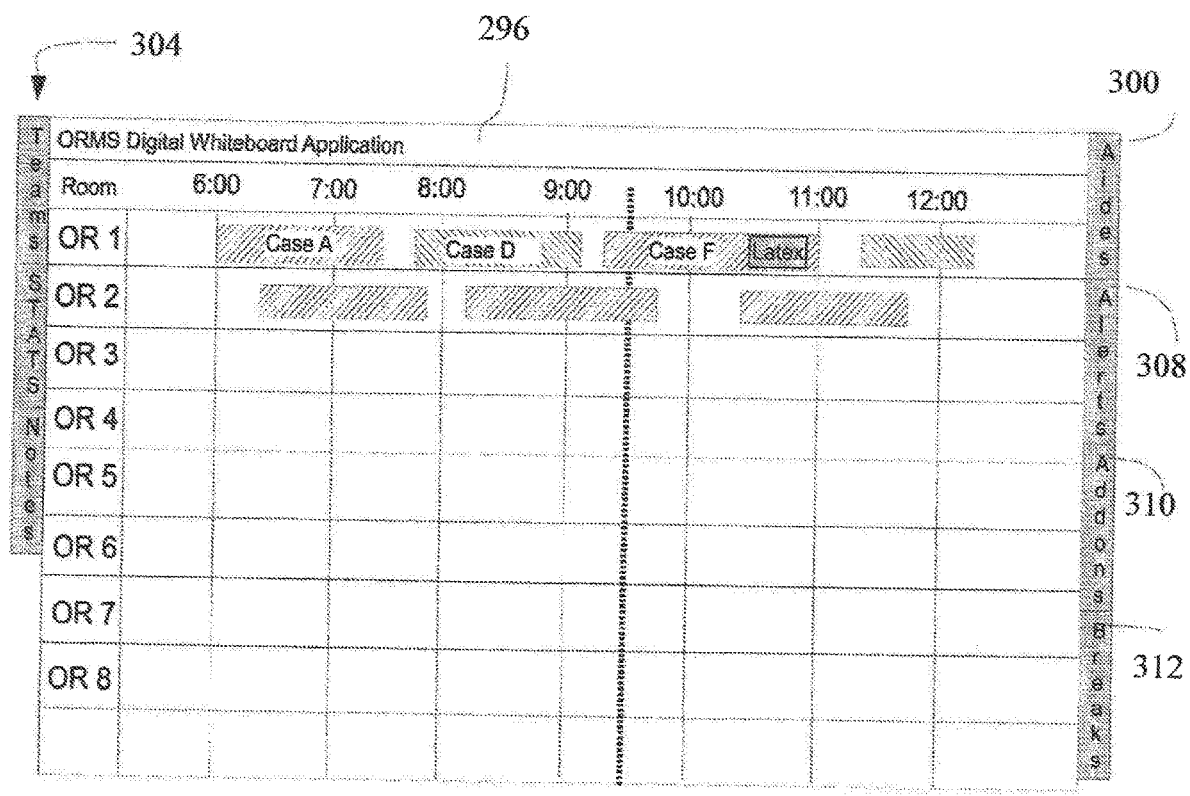
FIG. 15 is an illustration of tabs on the daily schedule display indicating the availability of viewable side panels.
Figure 16:
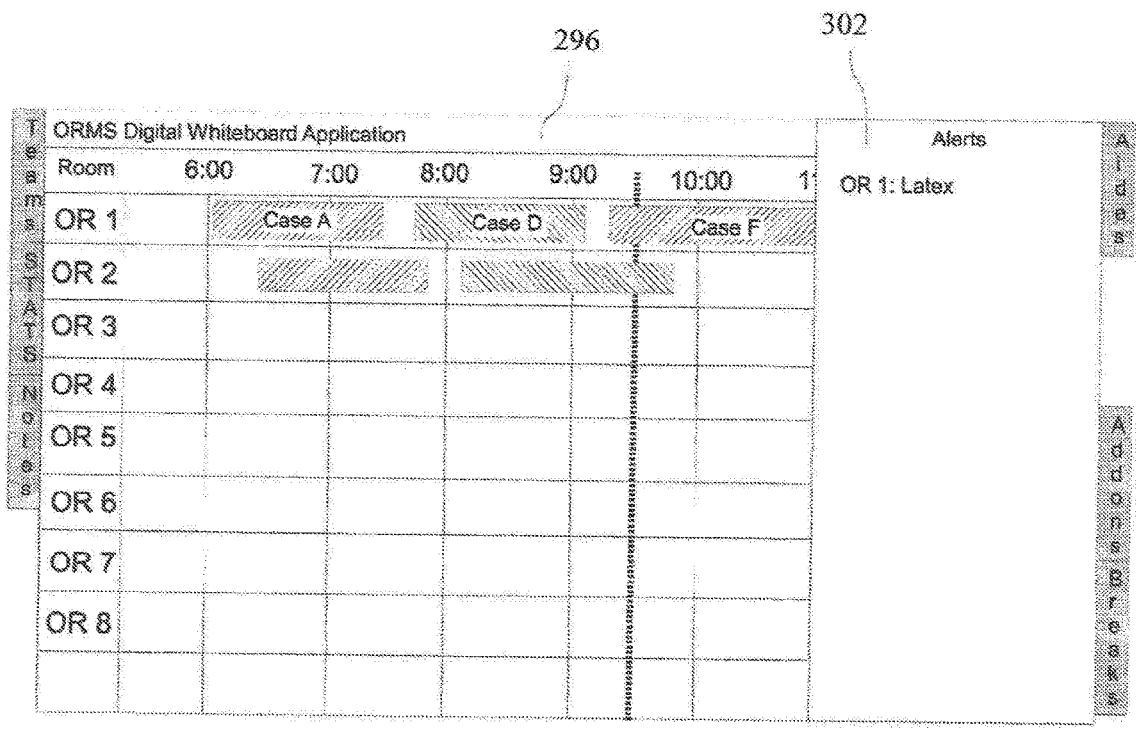
FIG. 16 is an illustration of a displayed side panel on the daily schedule display.

In another embodiment, FIGS. 15 to 18 illustrate dockable slide-out panels on the OR schedule. In FIG. 15, Tabs 300, 308, 310, and 312 arrayed on the right hand side of the daily schedule display 96 have labels indicating available panels with pertinent information. Other such tabs, as indicated at 304, are arrayed on left hand side of schedule 296. In FIG. 16, the Alerts tab 308 has been selected using for example, a computer mouse or touch screen entry, and the alert panel is displayed 302 while Alerts tab 308 temporarily disappears.

Information or notes can be added directly to panel 302 with digital input, for example, keyboard or computer mouse, and this information or notes is reproduced on some or all schedule displays through the hospital depending on user-selectable parameters. In an alternative embodiment, information or notes can be written directly in panel 302 area in an analog manner, that is, with a stylus or even a finger, and this information or notes is reproduced on some or all schedule displays throughout depending upon selectable parameters.

Figure 17:
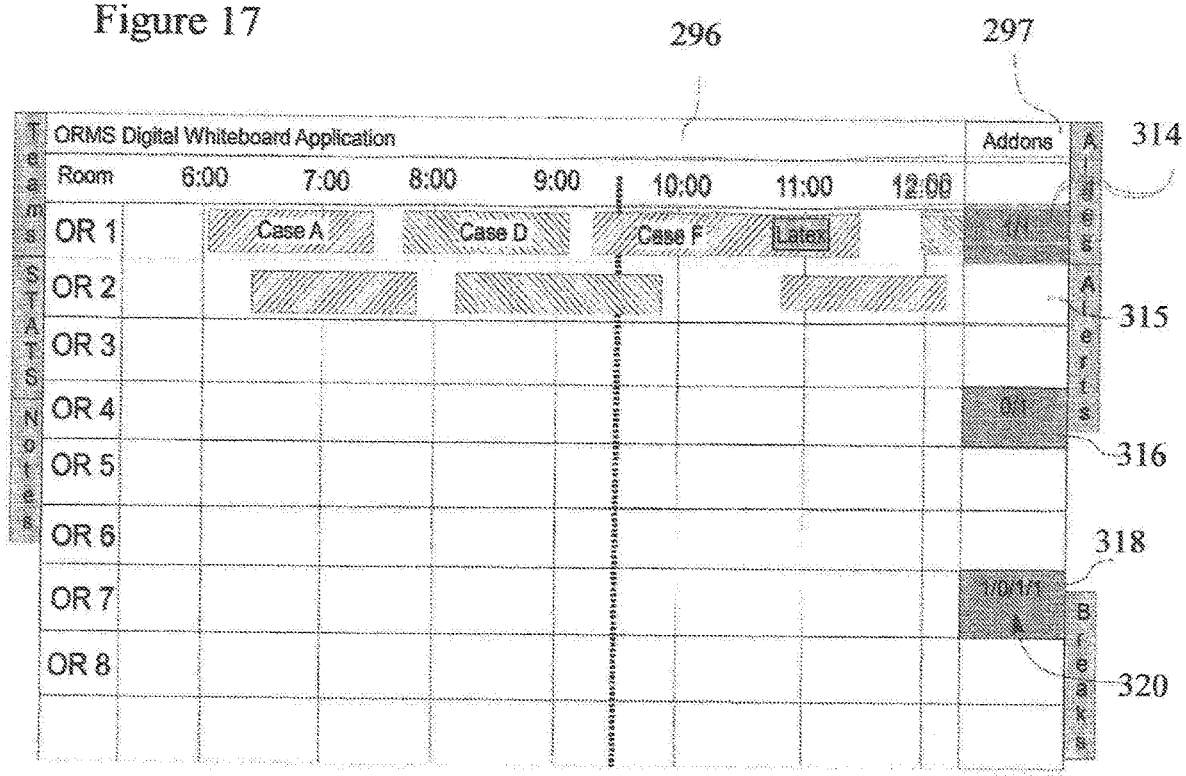
FIG. 17 is an illustration of a second displayed side panel on the daily schedule display.

FIG. 17 is an illustration of the schedule 96 when the Addons tab 310 has been selected such that the Addons panel 297 is displayed. An addon is a case which is newly added after the schedule for the day is created, with corresponding allocation of the hospital personnel and resources, and which is expected to run past a hospital's employee shift change time. Another type of addon is a case which was on the daily schedule when created but is delayed or running late due to unforeseen circumstances and is thus expected to run past the time of one or more employee shift changes. It is important for hospital managers and administrators to know quickly and accurately how many addon cases they have and through what shift changes they will go so they can make sure they will have the personnel present and resources on hand to cover these cases. A hospital or other health-care facility may have several shift change times when nurses, technicians, and other medical and administrative personnel end or start their work day. For example, a hospital might generally have four shift change times at 3:00 PM, 3:30 PM, 5:00 PM, and 7:00 PM.

For example, in FIG. 17, block 314 is highlighted to indicate there is one or more addon cases in OR 1. Block 116 is highlighted to indicate there is one or more addon cases in OR 4. And block 318 is highlighted to indicate there is one or more cases in OR 7. When no addon cases have been added to the schedule for an operating room, the corresponding addon block is not highlighted, for example, 315, and remains the neutral color of the schedule, typically white.

The highlighted addon blocks, 314, 316, and 318, contain a simple symbolic code, such as seen at 320 for example, which indicates how many addon cases are scheduled for the corresponding OR and the shift change times they are expected to run past. In this embodiment, the symbol 1 is used in the code to indicate an addon case that will run past a shift change. The position of the symbol 1 in the code indicates which shift change the addon case will run past. So in the case of a hospital with four employee shift changes at 3:00 PM, 3:30 PM, 5:00 PM, and 7:00 PM such as described hereinabove, the code would have up to four positions, reading from left to right. So for example, the code 320 has a 1 in first position indicating a case which will run past the earliest shift change time of concern, 3:00 PM. Then there is the symbol '/' as a separator and then the symbol 0 as a placeholder, indicating that there are no addon cases in OR 7 anticipated to run past the 3:30 PM shift change. Continuing to read from left to right at 320, there is a second '/' and then a 1 indicating that there is an addon case expected to run past the 5:00 PM shift change time. Finally, there is a '/' and a 1 indicating that there is an addon case expected to run past the 7:00 PM shift change. Note, it may or may not be that the addon case running past the 7:00 PM shift change is the same case or a continuation of the same case that is expected to run past the 5:00 PM shift change as described hereinabove.

Thus, the combination of color highlighting 314, 316, and 318, and a simple symbolic code 320, enables a hospital administrator or medical personnel manager to at a glance quickly and accurately determine the additional personnel and resources needed to timely complete, with optimum outcome, the cases the hospital has undertaken. That this combination of color highlighting and an associated simple symbolic code on a comprehensive, real-time updated daily schedule displayed or available to display at a multiplicity of locations throughout the hospital or healthcare facility, provides such facile comprehension of a possibly critical situation at hand, permitting quick and accurate decision making by perhaps a multiplicity of hospital or health-care facility administrators and managers at different locations, is a unique and surprising, perhaps even revolutionary, result.

Figure 18:
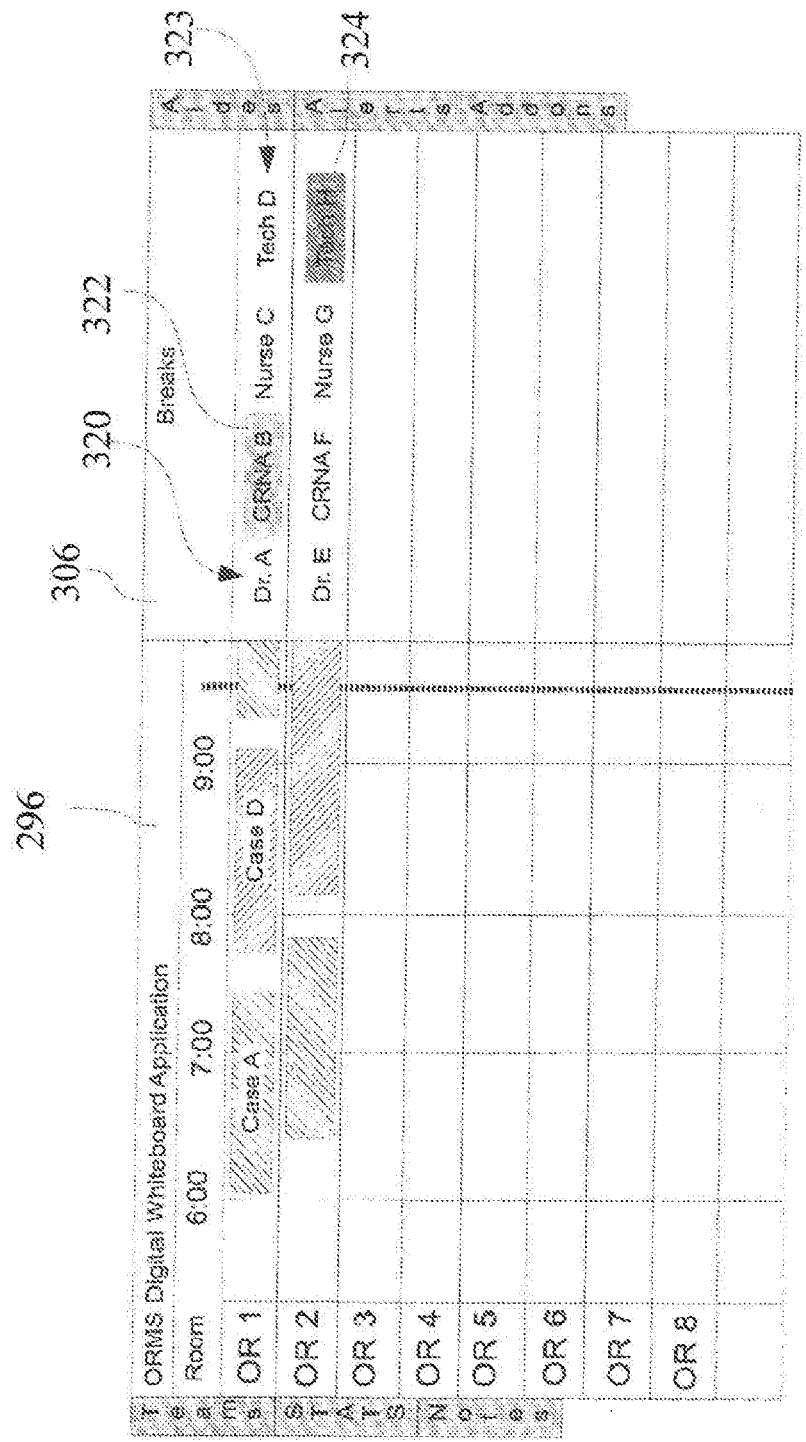
FIG. 18 is an illustration of a third displayed side panel on the daily schedule display.

FIG. 18 is an illustration of the schedule 296 when the Breaks tab 312 has been selected such that the Breaks panel 306 is displayed. A break is a relatively short period during the work shift of a hospital or healthcare facility employee when they are "off-duty", perhaps having a meal or a rest-break. The current break status of an employee is displayed and can be modified in the Breaks panel 306.

The personnel on a particular OR team are displayed in the row corresponding to the OR to which they are assigned such as indicated at 323. The name of team member not on break and working normally, indicated at 320 for example, will have a background of a neutral color, typically the same as the neutral color of daily schedule, typically white. A team member name can be selected, such as by clicking with a computer mouse or tapping with a finger or stylus on a touch-sensitive display, and then the background of the team member name will turn a color, for example 322, understood to indicate they are on break. A team member name can be selected a second time, and the background of their name will turn a second color, for example 324, understood to mean they have returned from break and are now working normally. After a set period, perhaps a few minutes, which can be configured by hospital administrators or other personnel, the second colored background 324 will automatically change back to the original neutral color indicating normal working status 320.

The organizational efficiency and decision making confidence gained by having all this information about the hospital's current patient cases available in a single view display of the daily schedule of the hospital is unique and surprising. However, while the hospital administrators, like the hospital medical personnel, benefit from having available comprehensive information about the hospitals current cases and relevant resources, not every administrator needs to have a continuous view of the schedule display.

FIGS. 19 and 20 are illustrations of a stoplight icon 330 which can be displayed on the computer desktop display 338 of administrators and at stations where the OR schedule display is not continuously needed. In a fashion similar to the workings of an ordinary traffic light for the control of street traffic, when there are no known problems likely to interfere with hospital's daily schedule as planned, the upper "lights" 332 and 334 would be dimmed and lower "light" 336 would be highlighted, typically green. If an alert condition occurs, which can be manually triggered or automatically triggered by calculation as described hereinabove, then light 336 would be dimmed and upper lights 334 or 332 typically would be yellow or red respectively, depending on the urgency of the alert.

As shown in FIG. 20 stop light icon 342 would typically be shown in a small window 340 on an administrator's PC desktop 338 but in other embodiments the icon could stand alone on the desktop without a surrounding window or in many other configurations as would be apparent to software engineers of ordinary skill in the art.

Figure 21:
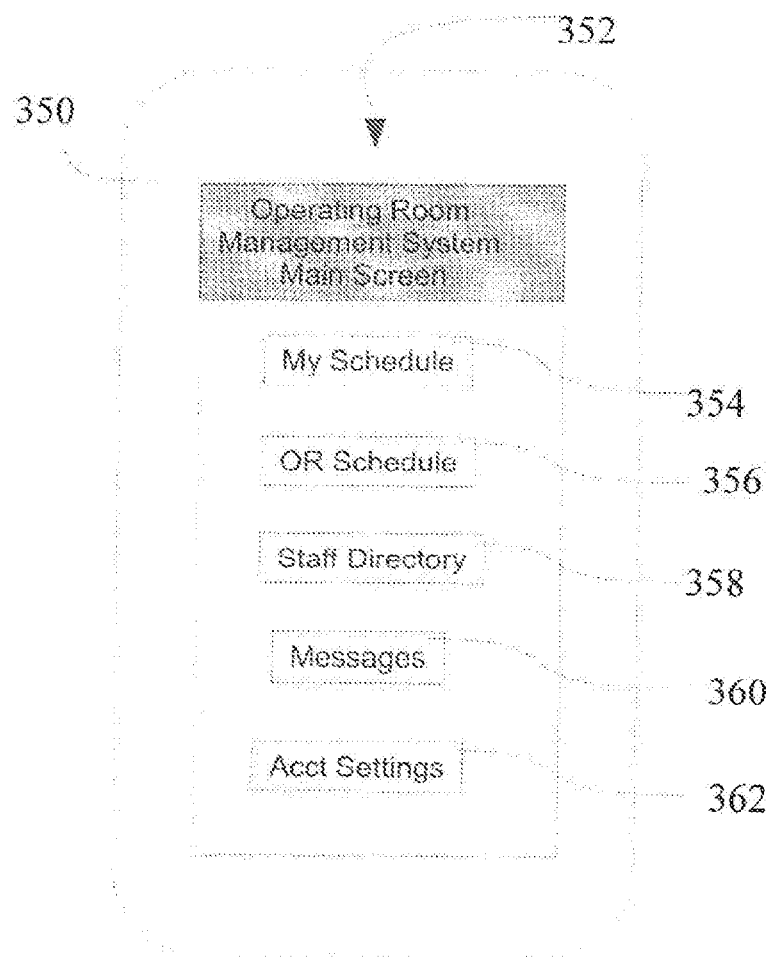
FIG. 21 is an illustration the main navigation display on the smartphone running the ORMS app of an embodiment.

FIG. 21 is an illustration of the main navigation screen of the ORMS app on the smartphone 350 of a user who might typically be a doctor or nurse at the hospital. The smartphone display indicated 352 shows selectable options to display the user's personal schedule 354, the OR daily schedule 356, the staff directory 358, the user's messages 360, and the user's account settings 362.

In another embodiment of the invention, a customized active cable arrangement is provided having at one end, a connector designed to mate with a specific medical device which transmits digital data that may be in a proprietary format, through said connector. At its other end, said cable arrangement is provided with a second connector, typically of a standard type, such as USB, PoE (Power Over Ethernet) for connecting with a supporting standard monitor for display.

Figure 22:
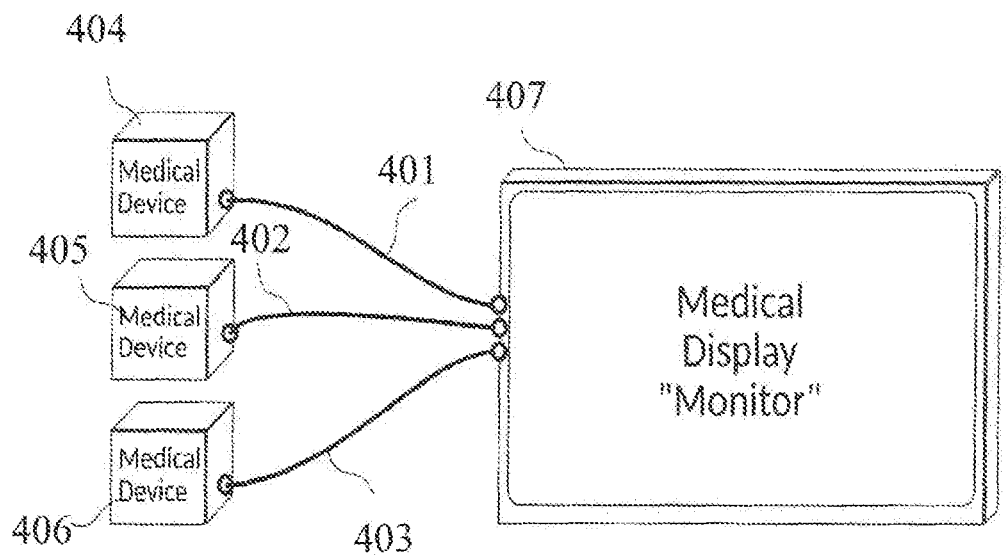
FIG. 22 is a block diagram of an embodiment of the invention wherein three active cables, each connected to a medical device, are plugged into a conventional monitor.

FIG. 22 is a block diagram overview of an embodiment of the customized active cable arrangement. According to the invention, medical devices 404, 405 and 406 are connected using corresponding active cable arrangements 401, 402, and 403 to a conventional medical display monitor 407. Note that the term "active cable arrangement" and "active cable" are used herein to describe the programmable dongle 412 and associated connectors and cables as will be explained in more detail below. In the example shown, medical devices 404, 405, or 406 can take on many different forms. Example medical devices include patient monitoring devices, blood analyzers, infusion pumps, ventilators, mobile EKG units, glucose analyzers, incubators, or other devices. Typically, "legacy" or third party medical devices lack an ability to be seamlessly integrated with a health care or hospital information system. The medical devices 404, 405, and 406 may have proprietary connectors (i.e., output ports having a non-standard physical arrangement) and/or transmit data in a proprietary format. In accordance with one aspect of the invention, the active cables 401, 402, and 403 of the invention are custom manufactured to order, both physically (if necessary) and with respect to the logic with which they are preprogrammed, for each corresponding medical device 404, 405, or 406. Thus, the user has the sensation of "plug and play" by simply connecting the medical device 404, 405, or 406 to an active cable 401, 402, or 403 of the invention to a conventional monitor USB port or USB hub extending the monitor USB port. The active dongle 412 of the invention is programmed to transform the proprietary data transmission protocol of the medical device 404, 405, or 406 and provide the monitor 407 (or other device) with standardized output for data, waveforms, alarms, setting, notifications, values and other useful information.

Instead of the general purpose processing capability of the usual intermediary PC or other intermediary electronic device, the active dongle 412 of the active cable arrangement of the invention has a dedicated, preprogrammed processing capability for transforming the data to a standard format for storage and display. The active dongle 412 is not easily susceptible to reprogramming or hacking. It is not expected that a software update would ever be required during the normal lifetime of the associated medical device as the data transmission protocol of the medical device 404, 405, or 406 will never change.

If a new medical device is added or replaces an older device, it is not necessary to install a new software driver on an intermediate PC (or equivalent), an uncertain prospect depending on the PC operating system, compatibility with other drivers/devices and many other details. Instead, along with placing into service a new medical device, a new active cable arrangement according to the invention is ordered and simply plugged in.

The supporting monitor 407 should support the display of the standardized and known, well documented values for data, waveforms, alarms, setting, notifications, values and other useful information from the USB dongle 412 of the invention, for example the software API and specifications of the normalized JSON protocol.

Prior to the invention, such medical devices 404, 405, or 406 would typically transmit data to an intermediary general purpose computer, for example, a conventional PC, for processing including display, analysis and recording. Such general purpose computers are commonplace and nominally inexpensive. But such PCs require continual maintenance including security and function upgrades. In well publicized incidents, computer hackers have halted or impeded the operations of health facilities, hospitals or entire health systems as a result of such intermediary PCs not having security upgrades implemented.

Figure 23:
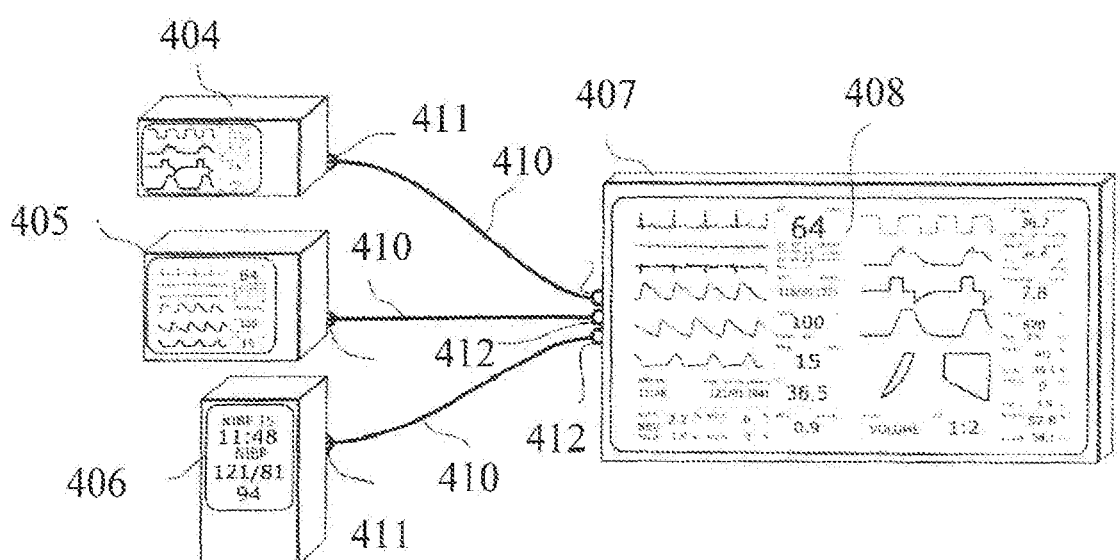
FIG. 23 illustrates the combined data displayed side-by-side and synchronously on a conventional medical monitor or from three medical devices connected to the monitor with active cables in an embodiment of the invention.

FIG. 23 illustrates the same-glass, side-by-side (or vertically arranged) synchronized display of the data transmitted by medical devices 404, 405 and 406. It should be noted here that the data transmitted by the medical devices 404, 405, and 406 will be displayed simultaneously on the monitor 7 in real time, even though the devices will be plugged into separate inputs. Preferably, monitor 7 is a standard medical monitor utilizing the JSON protocol. In an embodiment, connecting cables 10 do not have customized processing capability although they are equipped with conventional or proprietary connectors suitable for corresponding connected devices 404, 405, and 406. Instead, cables 410 plug into USB dongles 412 to form the cable arrangements 401, 402, and 403 of the invention, with each having customized processing capability corresponding to each connected medical device. USB dongles 412 in turn plug into conventional medical monitor 407. USB dongles 412 process the data from corresponding connected medical devices 404, 405 and 406, synchronizing it and formatting it for display 408 on monitor 407. The use of USB to connect to the dongle 412 to monitors is advantageous because it provides power to the dongle 412.

The active dongle 412 and associated connecting cables are built from standard parts by the manufacturer for the ordered medical device. Building the active cable assemblies 401, 402, or 403 from parts involves selecting the right connector and protocol for the device 404, 405, or 406, which protocol is written to the dongle 412 in a manner well known to those of skill in the art and then assembled and shipped to the user. The manufacturer does not need a skilled workforce.

Figure 24:
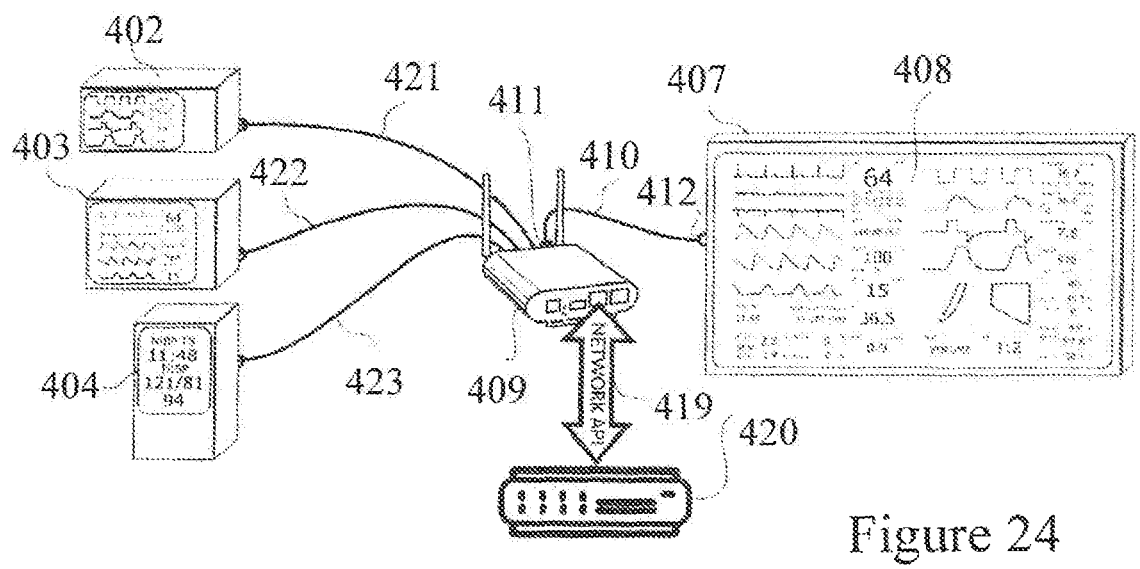
FIG. 24 is a diagram illustrating the connection of three medical devices with active cables to an IoT device enabling transmission of the medical device data to a remote server for permanent storage and/or analysis.

An intermediary IoT Connectivity Device 409 is used to facilitate recording in an embodiment illustrated in FIG. 24. An IoT Connectivity Device is a hardware device that enables physical and logical data transformation from proprietary and non-standardized protocols, to be collected and transformed into a standardized dataset. It also serves as a security and functional layer around the medical devices. As it has all the protocols implemented locally, it does not suffer from data loss (i.e., does not need to be reprogrammed or booted up) if the network is temporarily or otherwise unavailable. It is equipped with a battery and can be unplugged for significant periods, such as during transfer, or unforeseen power outages such as accidental connector detachment or temporary power failure, with full operational readiness. An IoT device used in the medical environment must be compliant with regulations imposed by law (for example with IEC EN 60601-1). TCP and UDP protocols and ports are used.

Ordinary cables 422, 423 and 424 connect medical devices such as 404, and for the purposes of FIG. 24 only, 402 and 403, to device 409. The device 409 formats the data for recording and uses Network API 19 to transmit the data to Hospital Information System 420. One should appreciate that the hospital information system 420 has a number of roles or responsibilities with respect to medical devices. One responsibility of the hospital information system 420 includes coordinating or managing activities of medical devices. The data formatted for display is then transmitted to conventional monitor 407 for display 408 via cable arrangement 401, 402, or 403 with optional USB dongle 412.

For example, in a hospital operating room (OR) during a typical 24 hours, patient monitors, anesthesia machines or ventilators, EEG monitoring, a BIS monitor and a few IV pumps will typically create 1 GB of data with perhaps a 60-85% compression ratio, resulting in a 150-400 MB encrypted repository for complete, high frequency datasets, including waveforms.

For an average ten hours of OR usage per day, and twenty four Hours ICU Monitor per patient, the twenty four hours encrypted, and compressed storage are expected to be in 80-120 MB range per bedside location.

Figure 25:
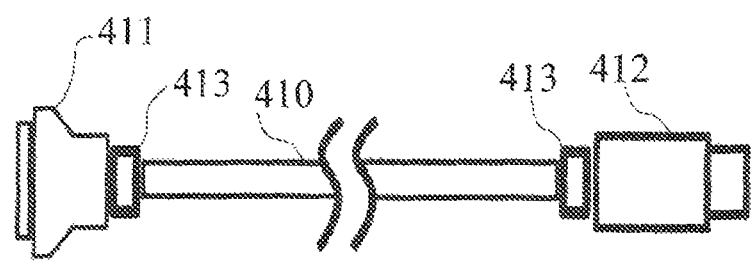
FIG. 25 is a block diagram showing the details of the physical construction of an active cable arrangement in an embodiment.

FIG. 25 is a block diagram illustrating the physical construction of the active cable arrangement of the invention in an embodiment. The active cables 401, 402, or 403 are manufactured to order for a specific, medical device such as 404, 405 or 406. Connector 411 may be standard or proprietary, specific to said device 404, 405, or 406. Connector 411 plugs into or otherwise connects to a standard RJ45 connector 413 which terminates both ends of a standard Cat 5 or Cat 6 Ethernet cable 410. The connector 413 opposite from said medical device 404, 405, or 406 plugs into USB dongle 412 which contains the processing capability and customized preprogrammed logic necessary to format for synchronized display data from said medical device. USB dongle 412 is powered by standard electrical output from the monitor 407 to which it is connected.

Figure 26:
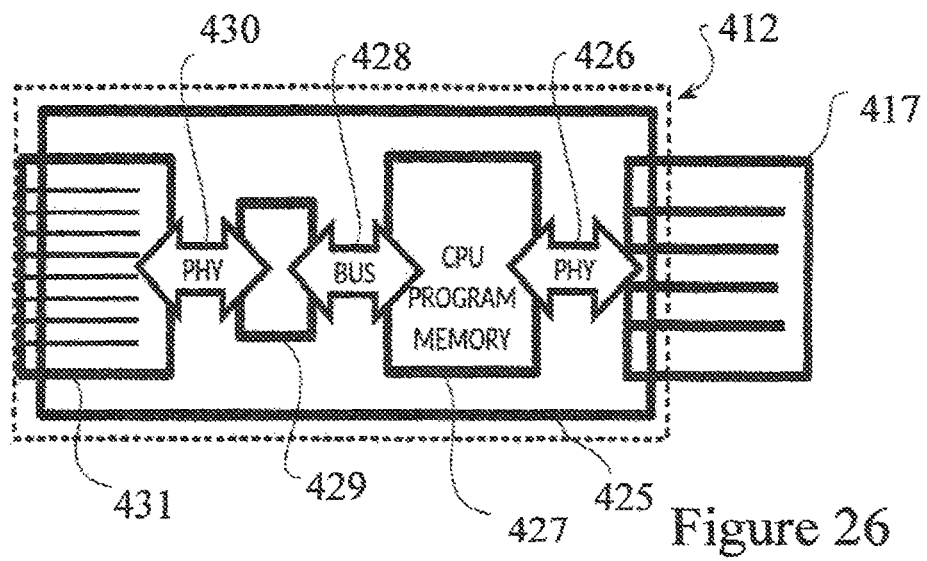
FIG. 26 is a block diagram illustrating the details of the logical processing capability of an active cable arrangement in an embodiment.

FIG. 26 is a block diagram illustrating the logical construction of the USB dongle 412 in an embodiment. Processor 427 receives power through USB standard connector 417 by which, dongle 412 is plugged into a monitor. Processing unit 429 receives data via medical device connector 431, converts proprietary data format to JSON key-value pairs, communicates using this standard format over bus 428 to processor 427 which synchronizes the data and otherwise prepares it for recording and display. As mentioned above, monitor 407 is a standard medical monitor and will automatically display the reformatted data from medical devices 404, 405, or 406 as standalone or in a combined time synchronized manner. The data from medical devices 404, 405, or 406 is not just displayable on monitor 407, it is transformed so as to be useable for any device. For example, data from device 404, 405, or 406 may be transmitted to hospital information center 420.

Figure 27:
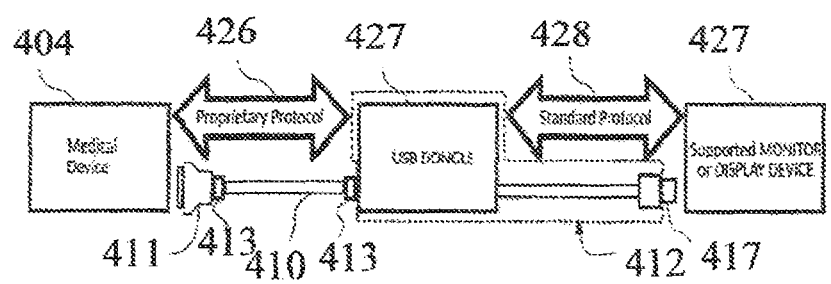
FIG. 27 is a block diagram illustrating the overall system and processing sequence in an embodiment.

FIG. 27 is a block diagram illustrating the cable arrangement and overall system in an embodiment. USB dongle 412 is connected to medical device 404 via a cable constructed as described in the description associated with FIG. 25 hereinabove. Dongle 412, a programmable microprocessor driven interface device, communicates with device 404 via proprietary protocol 426, uses its preprogramed logic to process the data into a standard format, and then transmits the processed data to monitor 407 using a standard protocol 428.

Figure 28:
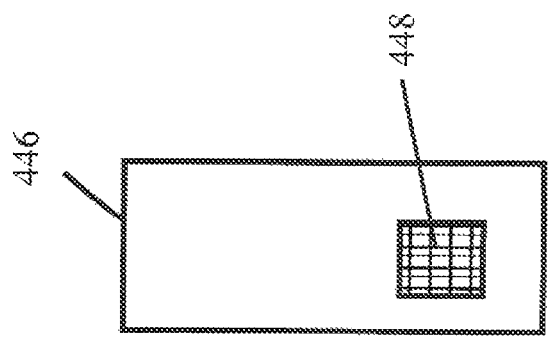
FIG. 28 is a graphical representation of the method of the invention in an embodiment illustrating the interconnection of the various computing resources necessary to produce the active cable arrangement of the invention.
Figure 28:
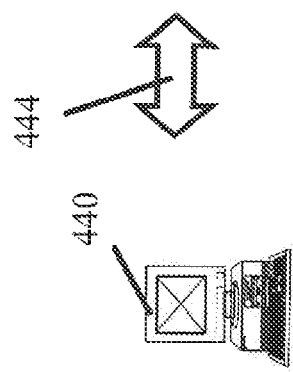

In another embodiment, the invention provides an automated method for providing a connecting cable arrangement 401, 402, or 403 for connecting a legacy or third party medical device such as 404, 405, or 406 having a proprietary connection arrangement or data transmission protocol (or both) to a standard medical monitor, from a manufacturer to an end user. In a preferred embodiment the method is implemented by way of a secure internet transaction. FIG. 28 shows a diagram representing principal equipment and key actions involved in a common internet purchasing transaction. A customer computing device 440 such as a PC, smart phone, tablet, or other device is operated by a user (not illustrated), for example, a person using his or her home or office computer. The customer has internet access via WiFi, or equivalent allowing the customer to communicate over the internet 444 to a large number of web sites. The customer accesses web sites of interest using the computing device 440. One web site is represented by a manufacturer 446 of the inventive active cable arrangement, the web site having data processing equipment including a server 448 for processing and saving data. Server 448 includes a database of known legacy medical devices. In accordance with the method, the end user would select a device of interest from a "drop down" list, a list of representative GUIs, or other means of displaying identifying information representing a list of medical devices/products stored on server 448. For each medical device listed, its transmission protocol and connection arrangement is known and stored on the server 448 but transparent to the user. The list is generated by the server 448 and can be transmitted over the internet 444 to the user for display on the user device 440 in response to a user request. If the user sees the desired medical device on the list he/she simply "clicks" on the device displayed on the list. Preferably, an actual image of the device (with the physical arrangement of the device output connector apparent) is stored on the server 448 and displayed in response to the click and the user can verify that the model selected is indeed the desired model. The user may then complete the transaction in the well known manner. Using the saved data regarding the selected device on server 448, which saved data will include the particular transmission protocol as well as the details of the particular connection arrangement of the selected legacy medical device, the manufacturer 446 will then provide or fabricate all of the cables and connectors necessary as discussed above, and program the dongle 412 with the appropriate software to generate an active cable arrangement such as 401, 402, or 403. The arrangement is then shipped to the user, who can then connect the medical device 404, 405, or 406 to the monitor 407 in "plug and play" fashion. The user need not further configure or program the cable arrangement or monitor 407.

If the user's desired medical device 404, 405, or 406 is not saved in the server 448 database, the user would provide either a specific model number and/or other information necessary for the manufacturer to determine the physical characteristics of the medical device connector as well as the data transmission protocol of the device. It should be noted that the above method is not limited to the examples shown, but can be used to retrofit any legacy or non-standard device for connectivity.

The invention could be used not only for display devices, but in general for any device, regulated medical devices as well, to receive standardized medical data from supported medical devices, if latter is equipped with standard USB connectivity and ability to read a standard protocol provided.

Although particular embodiments have been described in this disclosure, many other variations and modifications will be apparent to those skilled in the art. Thus, the instant invention can be defined and limited only by the claims to be associated with this application.

The invention claimed is:

1. A system for managing the display of a real time daily schedule, said schedule displayed in real time on a first type of display in operating rooms of a healthcare facility in a building and a second type of display on mobile phones, the system comprising:
   at least one server running a program having a set of data concerning the management of said operating rooms and being capable of displaying, on both said first and second display types; a real time daily schedule;
   a software interface for receiving and configuring the display of said real time daily schedule on said first display type;
   said schedule as displayed on said first display type comprises at least one block displaying an image having first, second, and third colored portions, said software interface selectively highlighting said first colored portion and dimming said second and third colored portions in response to a first scheduling scenario, said software interface highlighting either said second or third colored portions in response to an alert condition.

2. The system for managing the display of a real time daily schedule according to claim 1 wherein said server is further capable of communicating with at least one mobile phone which runs an application capable of alerting a mobile phone user.

3. The system for managing the display of a real time daily schedule according to claim 2 wherein the display by said application is of the daily schedule of the user.

4. The system according to claim 1 wherein said first display type in operating rooms are whiteboards, said whiteboards capable of receiving and displaying data which is input digitally to said whiteboards using a tablet computer and said whiteboards are further capable of receiving and displaying data which is input in an analog manner directly on the surface of the whiteboard.

5. The system according to claim 1 wherein the first display type in operating rooms of a healthcare facility in a building and the displays on mobile phones are capable of displaying a schedule for teams of healthcare facility personnel, said teams having been formed from a displayed list of healthcare facility personnel.

6. The system according to claim 2 wherein specific data input to said server will automatically trigger the sending of an alert to said user.

7. The system according to claim 2 wherein specific data input to said server will automatically trigger the texting of an alert to a user having a mobile phone.

8. A system for managing the operating rooms of a healthcare facility in a building, comprising:
   a cloud server running a program having a set of data concerning the management of said operating rooms and being capable of displaying a real time daily schedule for said operating rooms in said building, said cloud server including a mobile application server for receiving and transmitting said schedule as well as reports to mobile devices, said mobile devices having a first display type, said schedule and said reports based on real time analysis of said data;
   a hospital web server also receiving said schedule and reports from said cloud server;
   a software interface for receiving said schedule and reports from said hospital web server and configuring display of said schedule and said reports for a second display type;
   said schedule as displayed on said first display type comprises at least one block displaying an image having first, second, and third colored portions, said software interface selectively highlighting said first colored portion and dimming said second and third colored portions in response to a first scheduling scenario, said software interface highlighting either said second or third colored portions in response to an alert condition.

9. A system for managing the operating rooms of a healthcare facility according to claim 8 wherein said mobile application server is further capable of communicating with at least one mobile phone which runs an application capable of displaying said real time schedule and alerting a mobile phone user on said first display type.

10. A system for managing the operating rooms of a healthcare facility according to claim 9 wherein the display by said application on said second display type is of a daily schedule of the user.

11. A system according to claim 8 wherein said second display types are whiteboards in operating rooms, said whiteboards capable of receiving and displaying data which is input digitally to said whiteboards using a tablet computer and said whiteboards are further capable of receiving and displaying data which is input in an analog manner directly on the surface of the whiteboard.

12. A system according to claim 9 wherein the first and second display types are capable of displaying a schedule for teams of healthcare facility personnel, said teams having been formed from a displayed list of healthcare facility personnel.

13. A system according to claim 9 wherein specific data input to said server will automatically trigger the sending of an alert to said user.

14. A system according to claim 9 wherein specific data input to said server will automatically trigger the texting of an alert to a user having a mobile phone.

* * * * *

UNITED STATES PATENT AND TRADEMARK OFFICE
CERTIFICATE OF CORRECTION

PATENT NO.         : 11,532,393 B2
APPLICATION NO.    : 16/812282
DATED              : December 20, 2022
INVENTOR(S)        : Arkoff et al.

It is certified that error appears in the above-identified patent and that said Letters Patent is hereby corrected as shown below:

On the Title Page

Item (57) Line 1, Delete the entire text of the Abstract and replace with the following:
--A comprehensive health care data management system is provided. In an embodiment a system of servers is provided, which communicate data in real time with white boards stationed in the operating rooms of a healthcare facility. Medical personnel and healthcare facility staff members can view the formatted data on a white board and input new or revised data directly on the white board or at an input station near the white board.--

In the Claims

Column 22, Line 57, delete "said first display type" and insert --said second display type--

Signed and Sealed this
Eleventh Day of April, 2023

Katherine Kelly Vidal
*Director of the United States Patent and Trademark Office*